United States Patent [19]

Davis et al.

[11] Patent Number: 5,599,703

[45] Date of Patent: Feb. 4, 1997

[54] IN VITRO AMPLIFICATION/EXPANSION OF CD34+ STEM AND PROGENITOR CELLS

[75] Inventors: Thomas A. Davis, Chantilly, Va.; Steven Kessler, Cupertino, Calif.; Douglas H. Robinson, Washington, D.C.

[73] Assignee: The United States of America as represented by the Secretary of the Navy, Washington, D.C.

[21] Appl. No.: 142,569

[22] Filed: Oct. 28, 1993

[51] Int. Cl.⁶ .................... C12N 5/00; A01N 63/00; A01N 65/00

[52] U.S. Cl. .................... 435/373; 435/385; 435/386; 424/93.7

[58] Field of Search .................... 435/240.2, 240.21, 435/240.3; 424/93 U, 93.7

[56] References Cited

U.S. PATENT DOCUMENTS

| | | | |
|---|---|---|---|
| 4,714,680 | 12/1987 | Civin | 435/240.25 |
| 5,004,681 | 4/1991 | Boyse et al. | 435/2 |
| 5,061,620 | 10/1991 | Tsukamoto | 435/240.2 |
| 5,192,553 | 3/1993 | Boyse et al. | 424/529 |

OTHER PUBLICATIONS

Ascensao et al., Blood, 63: 553–558 (1984).
Brown et al., Blood, 82: 33–37 (1993).
Brugger et al., Blood, 81: 2579–2584 (1993).
Deryugina et al., Critical Rev. In Immunology, 13(2): 115–150 (1993).
S. M. Edgington, Biotechnology, 10: 1099–1106 (1992).
Islam et al., The Anatomical Record, 233: 440–452 (1992).
Issaad et al., Blood, 81: 2916–2924 (1993).
Koller et al., Blood, 82: 378–384 (1993).
Mayani et al., Eur. J. Haematol., 49: 225–233 (1992).
Negrin et al., Marrow Transplantation Reviews, 2: 23–26 (1992).
K. H. Antman, Marrow Transplantation Reviews, 2: 27–32 (1992).
Monroy et al., Int. Journal of Cell Cloning, 10: 105–115 (1992).
Palsson et al., Biotechnology, 11: 368–372 (1993).
Robinson et al., In Vitro Cell. Dev. Biol., 26: 169–180 (1990).
Robinson et al., Blood, 77: 294–305 (1991).
Rowley et al., Blood, 82: 60–65 (1993).
Schwartz et al., Proc. Natl. Acad. Sci. USA, 88: 6760–6764 (1991).
Srour et al., Blood, 81: 661–669 (1993).
Toksoz et al., Proc. Natl. Acad. Sci. USA, 89: 7350–7354 (1992).
Broxmeyer et al, Proc. Natl. Acad. Sci USA, vol. 86, pp. 3828–3832 (1989).
Broxmeyer et al, Bone Marrow Transplantation, vol. 9 (Supp. 1) pp. 7–10 (1992).
Carow et al, Blood, vol. 81, No. 4, pp. 942–949 (Feb. 15, 1993).
Broxmeyer et al, Proc. Natl. Acad. Sci USA, vol. 89, pp. 4109–4113 (1992).

*Primary Examiner*—Michael G. Wityshyn
*Assistant Examiner*—Kristin K. Larson
*Attorney, Agent, or Firm*—A. David Spevack; William Garvert

[57] ABSTRACT

The present invention relates to a method of amplifying in vitro stemcells. In this method hematopoietic CD34+ stem and progenitor cells are isolated from human bone marrow and contacted with endothelial cells. The contacted stem cells and endothelial cells are cultured in the presence of at least one cytokine in an amount sufficient to support amplification/expansion of the hematopoietic CD34+ stem and progenitor cells. This method produces increased yields of hematopoietic CD34+ stem and progenitor cells which can be used in human therapeutics.

9 Claims, 11 Drawing Sheets

PANEL A

PANEL B

IN VITRO AMPLIFICATION/EXPANSION OF CD34+ STEM AND PROGENITOR CELLS

BACKGROUND OF THE INVENTION

1. Field of the Invention

The present invention relates to a method of amplifying/expanding hematopoietic stem cells. In particular, the present invention relates to the amplification/expansion of human bone marrow stem cells by culturing cells with endothelial cells in the presence of growth factors or cytokines.

2. Description of the Prior Art

Hematopoiesis, the formation of mature blood cells, involves a complex scheme of multilineage differentiation (Metcalf, *Nature* 339:27–30, 1989). Hematopoiesis occurs mainly in the bone marrow where hematopoietic stem cells (pluripotential stem cells) proliferate and differentiate into progenitor cells which then develop into different types of mature blood cells (Gordon et al., *Bone Marrow Transplant* 4:335, 1989; Dexter et al., *Ann. Rev. Cell Bio.* 3:423, 1987). The hematopoietic stem and progenitor cell is functionally characterized by its extensive and prolonged self-renewal capacity as well as its ability to differentiate and thereby give rise to cells of all lymphohematopoietic lineages (Sprangruide et al., *Science* 241:58, 1988; Terstappen et al., *Blood* 77:1218, 1991; Civin et al., *Exp. Hematol.* 15:10, 1987; Civin et al., *J. Immunol.* 133:157, 1984; Strauss et al., *Exp. Hematol.* 14:878, 1986). Phenotypically, the only well defined human hematopoietic stem and progenitor cell marker at present is the CD34 hematopoietic cell surface antigen (Civin et al., *J. Immunol.* 133:157, 1984; Strauss et al., *Exp. Hematol.* 14:878, 1986). This cell surface antigen is a highly glycosylated 115-Kd type I integral membrane protein of unknown function (Civin, *Exp. Hematol.* 18:461, 1990). The sequence of the human CD34 cDNA suggests the presence of several O-linked glycosylation sites (Simmons et al., *J. Immunol.* 148:267, 1992) and that the attachment of lineage-specific glycans to the CD34 backbone may permit binding to lectins on marrow stromal cells or the extracellular matrix. The CD34 antigen is expressed by approximately 1–5% of the human bone marrow cell population (Civin et al., *Exp. Hematol.* 15:10, 1987; Civin et al., *J. Immunol.* 133:157, 1984; Strauss et al., *Exp. Hematol.* 14:878, 1986) and include pluripotent as well as precursors for each of the hematopoietic cell lineages (Andrews et al., *J. Exp. Med.* 172:355, 1990; Berstein et al., *Blood* 77:2316, 1991). In addition, the CD34 antigen is expressed on human vascular endothelial cells (Fina et al., *Blood* 75:2417, 1990), suggesting a possible role for the antigen in adhesion or cellular interactions. Purified CD34+ stem and progenitor cells can reconstitute hematopoiesis in vivo (Berenson et al., *J. Clin. Invest.* 81:951, 1988; Berenson, et al., *Blood* 77:1717, 1991) and support myelopoiesis for several months in association with stromal cells in long-term bone marrow cultures (Allan et al, *Exp. Hematol.* 12:517, 1984; Andrews et al, *J. Exp. Med.* 172:355, 1990; Sutherland et al, *Blood* 74:1563, 1989; Gordon et al, *J. Cell Physiol.* 130:150, 1987; Gordon et al, *Br. J. Haematol.* 60:129, 1985; Verfaillie et al, *J. Exp. Med.* 172:509, 1990). Additional studies have demonstrated that the pluripotent hematopoietic stem cell can be identified by additional phenotypic markers, singly and in combination. The most primitive pluripotent human bone marrow hematopoietic stem cells are small (low forward light scatter and side scatter) CD34+, Thy1+/−, c-kit+, HLA-DR−, CD38−, CD15−, rhodamine-123 dull and 4-hydroperoxycyclophosphamide-resistant cells, but are hematopoietic lineage marker negative (Lin−) (Baum et al, *Proc Natl Acad Sci USA* 89:2804, 1992; Briddle et al, *Blood* 79:3159, 1992; Craig et al, *J Exp Med* 177:1331, 1993). Similarly, recent purification experiments have shown that the most primitive murine hematopoietic stem cells have been isolated with the use of a variety of phenotypic markers, such as Thy-1, c-kit, wheat-germ agglutinin (WGA), and stem cell antigen (Okada et al, *Blood* 78:1706, 1991; Ikuta and Weissman, *Proc Natl Acad Sci USA* 89:1502, 1992) but are Lin− (Sprangrude et al, *Science* 241:58, 1988).

The bone marrow serves in vivo as the requisite microenvironment where constitutive hematopoiesis, stem cell differentiation and stem cell self-renewal occurs (Gordon et al., *Bone Marrow Transplant* 4:335, 1989; Dexter et al., *Ann. Rev. Cell Bio.* 3:423, 1987; Allan et al., *Exp. Hematol.* 12:517, 1984). This microenvironment has two major components—the lymphohematopoietic elements and the bone marrow stroma. The bone marrow stroma, made up of fibroblasts, endothelial cells, adipocytes and macrophages/monocytes, provides a heterogeneous adherent cell layer. Only these heterogeneous adherent cell layers have been shown to be effective in supporting long-term in vitro CD34+ stem and progenitor cell proliferation and differentiation (Dorshkind, *Annu. Rev. Immunol.* 8:111, 1990; Dexter et al., *J. Cell Physiol.* 91:335, 1977; Allan et al., *Exp. Hematol.* 12:517, 1984). Within the bone marrow stroma, CD34+ hematopoietic stem and progenitor cells undergo self-renewal, proliferation and differentiation (Andrews et al., *J. Exp. Med.* 172:355, 1990; Sutherland et al., *Blood* 74:1563, 1989; Gordon et al., *J. Cell Physiol.* 130:150, 1987; Gordon et al., *Br. J. Haematol.* 60:129, 1985). The proliferation and differentiation of CD34+ stem and progenitor cell in stromal dependent cultures is thought to involve cell-to-cell interactions (Andrews et al., *J. Exp. Med.* 172:355, 1990; Verfaillie et al., *J. Exp. Med,* 172:509, 1990; Gordon et al., *J. Cell Physiol.* 130:150, 1987), stroma derived cytokines (Berstein et al., *Blood* 77:2316, 1991; Dorshkind, *Annu. Rev. Immunol.* 8:111, 1990; Dexter et al., *J. Cell Physiol.* 91:335, 1977; Clark et al., *Science* 236:1229, 1987) and extracellular matrix proteins (Campbell et al., *J. Clin. Invest.* 75:2085, 1985; Campbell et al., *Nature* 329:744, 1987; Tsai et al., *Blood* 69:1587, 1987; Liesveld et al., *Blood* 73:1794, 1989).

There has been much interest and work in establishing an in vitro culture system for CD34+ hematopoietic stem and progenitor cells (Edgington et al., *Bio/Technology* 10:1099, 1992). CD34+ hematopoietic stem and progenitor cells cultured in vitro could be used in human therapeutics. For example, such cells could be employed in bone marrow transplantation (BMT). Most BMT protocols attempt to restore hematopoietic function following exposure to myeloablative agents. BMT is, therefore, an important adjunct to the therapeutic treatment of advanced malignancies (both hematologic and non-hematologic), intrinsic marrow defects, and bone marrow injury by extrinsic agents (for example, radiation or toxins). In addition, BMT in combination with developing genetic therapy technology is expected to play an increasing role in the treatment of numerous diseases. For a general review, see Negrin et al. (*Marrow Transplantation Reviews* 2:23, 1992) and Antman (*Marrow Transplantation Reviews* 2:27, 1992).

Hematopoietic culture systems can be broadly classified into two groups, liquid culture and stromal coculture systems. Liquid culture systems grow CD34+ hematopoietic stem and progenitor cells suspended in liquid media with additional growth factors and cytokines (Haylock et al, Blood 80: 1405, 1992; Brugger et al, Blood 81: 2579, 1993). Although liquid cultures are easy to maintain and are technically well suited for large scale expansion of CD34$^+$ hematopoietic stem and progenitor cells for use in therapy, they have uniformly been unsuccessful in generating expanded numbers of CD34$^+$ stem and progenitor cells that are necessary for long term engraftment. This is also reflected in the fact that it is difficult to maintain these cultures over a long period of time (months) as the CD34$^+$ stem cells all quickly differentiate into more mature cells. The inability to maintain and expand a proliferating pool of undifferentiated CD34$^+$ stem and progenitor cells is thought to be due to the lack of the appropriate microenvironment generated by the bone marrow stromal elements. To rectify this problem, stromal coculture systems grow CD34$^+$ hematopoietic stem and progenitor cells on or within an adherent layer of bone marrow stroma (a heterogeneous population of endothelial cells, adipocytes, fibroblasts and macrophages), with or without the addition of growth factors and cytokines.

One of the first long-term bone marrow culture systems (LTBMCS) was described by Dexter et al., (Dexter et al., Ann. Rev. Cell Bio. 3:423, 1987). Dexter et al.'s LTBMCS demonstrated that sustained cellular growth and development can be accomplished under in vitro culture conditions. In this system, an adherent bone marrow stromal layer appears to provide the growth factors and cellular environment necessary for the proliferation of CD34$^+$ hematopoietic stem and progenitor cells and their differentiation into a variety of committed progenitor cells (Andrews et al., J. Exp. Med. 172:355, 1990; Gordon et al., Br. J. Haematol. 60:129, 1985). However, the microenvironmental influences and regulation of hematopoiesis in this culture system are difficult to analyze due to the heterogeneity of the cell types that make up the bone marrow stroma. This complexity of the microenvironment also greatly hinders attempts to define elements that are responsible for specific stages of hematopoietic cell development.

Despite the ability of LTBMCS to generate a sustained output of cells over a long period (indicating the maintenance of a CD34$^+$ stem and progenitor cell pool), these systems are presently difficult to utilize in a therapeutic setting. First, there is the aforementioned complexity of the heterogeneous cellular microenvironment which confounds careful analysis of the ongoing biological mechanisms and prevents substantial improvement of the culture system. Second, LTBMCS require the establishment of a bone marrow stromal layer prior to the seeding of hematopoietic cells into the culture. Establishment of the stromal layer often takes weeks, a significant delay. This also hinders large scale LTBMCS which will be required for therapeutic applications. Finally, there is not a rapid and significant output of CD34$^+$ hematopoietic stem and progenitor cells from these culture systems, again limiting their usefulness in the therapeutic setting.

In an effort to overcome the complexity and the limitations of the Dexter LTBMCS, perfusion bioreactor systems were developed in which CD34$^+$ hematopoietic stem and progenitor cells could be cultured. Perfusion bioreactors help to maintain a defined culture environment and reduce physical disruption. See, for example, Schwartz et al. (PNAS USA 88:6760, 1991), Koller et al. (Bio/Technology 11:358, 1993), Koller et al. (Blood 82:378, 1993), and Palsson et al. (Bio/Technology 11:368, 1993). However, most of these perfusion bioreactor systems are modified liquid culture systems and suffer many of the same shortcomings in their inability to amplify/expand the pluripotent hematopoietic CD34$^+$ stem and progenitor cell pool, cells essential for long term/permanent engraftment and reconstitution of the hematopoietic system. This limits the usefulness of these culture systems for bone marrow transplantation and gene therapy of CD34$^+$ hematopoietic stem and progenitor cells.

Thus, the need for in vitro culture systems capable of clinically useful amplification of human CD34$^+$ hematopoietic stem and progenitor cells as well as other hematopoietic elements continues. A system capable of producing large quantities of certain bone marrow elements is needed to supply sufficient quantities of these elements for use in human therapeutics, for example, as bone marrow transplantation, transfusable blood components or genetic therapy.

SUMMARY OF THE INVENTION

Accordingly, it is one object of the present invention to provide a method of amplifying/expanding in vitro human hematopoietic CD34$^+$ bone marrow stem and progenitor cells which provides sufficient quantities of CD34$^+$ stem and progenitor cells for human therapeutic use. This unique culture system allows those skilled in the art the opportunity to examine the events controlling CD34$^+$ stem and progenitor cell proliferation, self-renewal, and commitment in an environment that mimics the in vivo situation. This hematopoietic CD34$^+$ stem and progenitor cell amplification/expansion technology can be used to rapidly generate sufficient numbers of progenitors and postprogenitor cells for clinical application in bone marrow transplantation and for use in gene therapy. In addition, manipulation of specific elements of the culture conditions (i.e. cytokines used, etc.) may result in the lineage commitment of the CD34$^+$ stem and progenitor cell progeny to differentiate into specific marrow elements. The ability to CD34$^+$ bone marrow stem and progenitor cells towards mature functional blood cells, such as granulocytes or platelets, would provide a powerful therapeutic modality. In addition, the capability of this system to rapidly and significantly amplify/expand primitive CD34$^+$ hematopoietic stem and progenitor cells provides an attractive system for transduction/transfection of primitive CD34$^+$ hematopoietic stem and progenitor cells for gene therapy.

It is another object of the present invention to provide a cell culture system to determine optimal culture conditions, growth factor combinations, feeding schedules and bioreactor configurations for maximal nonadherent cell proliferation, CD34$^+$ stem and progenitor cell amplification/expansion, and multipotential colony-forming cell activity (i.e. LT-IC, CFU-BLAST, CFU-MIX, and CFU-GM) using unseparated mononuclear cells, Lin$^-$ cells and purified CD34$^+$ stem and progenitor cells from patient and normal bone marrow aspirates, peripheral blood and cord blood.

It is also an object of the present invention to provide a culture system to selectively amplify/expand primitive CD34$^+$ hematopoietic stem and progenitor cells and test, in hematopoietic animal models (rodent, and primate) which mimic radiation or chemical induced myelosuppression, the short-term and long-term hematopoietic reconstitution potential of those cells generated via various stem and progenitor cell amplification/expansion and transfusion technologies. Specifically, the recovery kinetics of peripheral blood progenitor cells, bone marrow cell progenitors and their mature cell progenies can be tested. In addition, the long-term in vivo repopulating potential of CD34$^+$ stem and progenitor cells (LT-IC) generated can be assayed in severe combined immunodeficiency (SCID) mice and also by surgically implanting these cell in utero into fetal sheep with the level of hematopoietic engraftment determined at various intervals of gestation.

It is also an object of the present invention to provide a cell culture system to selectively amplify/expand normal hematopoietic CD34+ stem and progenitor cells separated from leukemic cells in leukemic patients prior to chemotherapy and autologous bone marrow transplantation.

It is another object of the present invention to provide a cell culture system which permits proliferation and amplification/expansion of hematopoietic CD34+ stem and progenitor cells, and allows for their transduction or transfection with gene constructs for use in gene therapy and related practices.

It is a further object of the present invention to provide a large scale bioreactor cell culture system for Phase I clinical trials (CD34+ stem and progenitor cell amplification/expansion and autologous BMT following marrow ablation). This large-scale technology can be implemented to reduce the morbidity, mortality, cost, hospitalization, and patient management associated with standard therapy, but also to investigate more aggressive therapy protocols and therapy compression schedules so that a greater proportion of patients survive cancer.

It is another object of the present invention to provide a cell culture system which permits better characterization of molecular mechanisms and cellular interactions involved in the regulation of hematopoietic CD34+ stem and progenitor cell self-renewal and commitment to differentiation of populations derived therefrom.

It is a further object of the present invention to provide a culture system which permits improved evaluation of the role of direct stromal or accessory cell contact and/or derived factors in modulating the proliferation and differentiation of various subsets of CD34+ hematopoietic stem cells, progenitor and precursor cells precursor cells.

It is also an object of the present invention to provide a cell culture system which enables amplification/expansion and isolation of specific developmentally defined subsets of hematopoietic cells to facilitate analysis and manipulation of genetic or other molecular elements involved in hematopoietic stem cell self renewal and differentiation.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention in one embodiment comprises a method of amplifying/expanding in vitro human bone marrow CD34+ stem and progenitor cells. The method comprises isolating CD34+ stem cells from human bone marrow; contacting the isolated stem and progenitor cells with endothelial cells; and culturing the stem and progenitor and endothelial cells in the presence of at least one cytokine in an amount sufficient to support amplification/expansion of the CD34+ stem and progenitor cells.

In another embodiment, the present invention comprises a method of engrafting CD34+ stem and progenitor cells in a patient. In this CD34+ stem and progenitor cells are first isolated from human bone marrow. Then, the CD34+ stem and progenitor cells are contacted with endothelial cells and the combination is cultured in the presence of at least one cytokine in an amount sufficient to support amplification/ expansion of the CD34+ stem and progenitor cells. After amplification/expansion, the CD34+ stem and progenitor cells are isolated from the culture and infused into the patient.

In another embodiment, the present invention comprises a method of engrafting more differentiated hematopoietic cells in a patient to allow for the rapid, short term reconstitution of mature blood cells in the circulation. In this method CD34+ stem and progenitor cells are first isolated from human bone marrow. Then, the CD34+ stem and progenitor cells are contacted with endothelial cells and the combination is cultured in the presence of at least one cytokine in an amount sufficient to support amplification/expansion and differentiation of the CD34+ bone marrow stem and progenitor cells. After amplification/expansion, the whole population of CD34+ stem and progenitor cells as well as more differentiated cells is infused into the patient.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
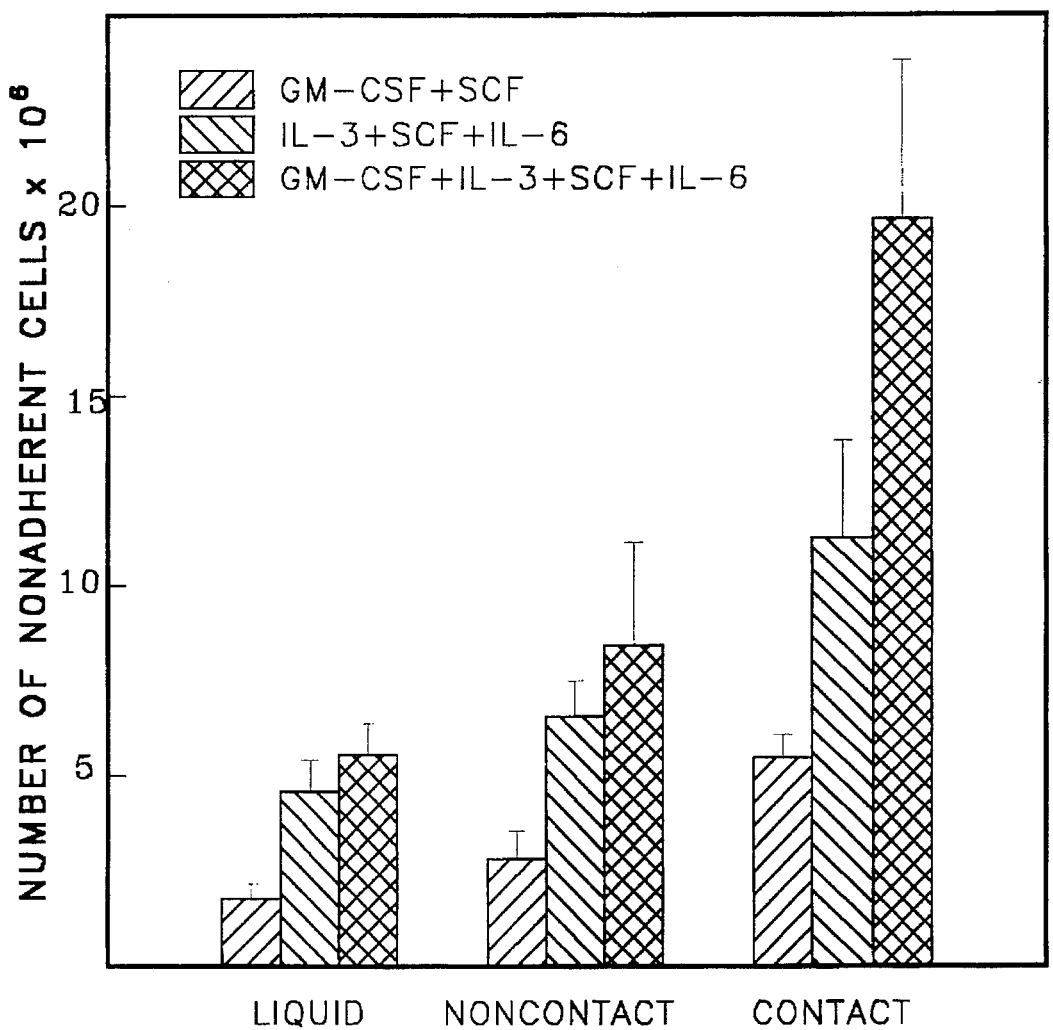
FIG. 1 shows the effects of optimal concentrations of granulocyte-macrophage colony stimulating factor (GM-CSF)+stem cell factor (SCF), interleukin-3 (IL-3)+SCF+ interleukin-6 (IL-6), and GM-CSF+IL-3+SCF+IL-6 on the production of nonadherent cells in liquid suspension cultures (n=6), noncontact porcine brain microvascular endothelial cells (PMVEC) cultures (n=6), and contact PMVEC cultures (n=12). Each column represents the mean number of total viable nonadherent cells±1SD harvested after 7 days of culture per 1×10$^5$ human CD34+ bone marrow stem and progenitor cells initially cultured. Results from five different experiments are depicted.

The present invention relates to an in vitro culture system that supports the proliferation and amplification/expansion of both primitive hematopoietic bone marrow blood stem cells ($CD34^+$ $CD38^-$) and $CD34^+$ progenitor cells for all hematopoietic cell lineages. Using endothelial cells treated with cytokines, a culture system was developed which supports primitive hematopoietic stem cell amplification/expansion. In this culture system, isolated $CD34^+$ stem and progenitor cells in contact with endothelial cells are cultured in the presence of cytokine(s) to promote the proliferation and amplification/expansion of the $CD34^+$ stem and progenitor cells.

The pluripotent hematopoietic stem cell can be defined functionally as well as phenotypically. Functionally, stem cells are those hematopoietic cells having the capability for prolonged self-renewal as well as the ability to differentiate into all the lymphohematopoietic cell lineages. Thus pluripotent hematopoietic stem cells, when localized to the appropriate microenvironment, can completely and durably reconstitute the hematopoietic and lymphoid compartments. Multilineage stem and progenitor cells can also be identified phenotypically by cell surface markers. A number of phenotypic markers, singly and in combination, have been described to identify the pluripotent hematopoietic stem cell. Primitive human stem cells have been characterized as small cells which are $CD34^+$, $CD38^-$, $HLA-DR^-$, $Thy1^{+/-}$, $CD15^-$, $Lin^-$, $c-kit^+$, 4-hydroperoxycyclophosphamide-resistant and rhodamine 123 dull. Equivalent primitive murine stem cells have been characterized as $Lin^-$, $Sca^+$, and $Thy1.1^+$. Preferably, the human $CD34^+$ stem cells used in the present culture system are $CD34^+$ $CD38^-$.

The $CD34^+$ stem and progenitor cells used in the present culturing method can be isolated from bone marrow, peripheral blood, or umbilical cord blood using methods known in the art. As the present culturing method is useful for amplifying/expanding stem cells from various species, the stem and progenitor cells can be isolated from, for example, humans, non-human primates or mice. The stem and progenitor cells utilized in the present method are preferably substantially enriched, that is, depleted of mature lymphoid and myeloid cells. Preferably, the $CD34^+$ stem and progenitor cells are enriched at least 85%, more preferably at least 95%, and most preferably at least 99%. Several methods by which $CD34^+$ stem and progenitor cells can be isolated and enriched to high degrees of purity using positive immunoselection have been described by Berenson et al (*Journal of Immunological Methods*, 91:11–19, 1986), Thomas et al (*Prog Clin Biol Res* 377:537–44, 1992), and Okarma et al (*Prog Clin Biol Res* 377:487–502, 1992).

In the present culture system, the enriched $CD34^+$ stem and progenitor cells are placed in direct contact with endothelial cells. Preferred endothelial cells are brain microvascular endothelial cells, more particularly, porcine brain microvascular endothelial cells (PMVEC). Examples of other endothelial cells suitable for use in the present invention include, but are not limited to, human endothelial cells, microvascular endothelial cells, brain endothelial cells, porcine endothelial cells and various types of immortalized endothelial cells.

It is important that the $CD34^+$ stem and progenitor cells be in contact with the endothelial cells to maximize amplification/expansion. For example, the $CD34^+$ stem and progenitor cells can be seeded onto a 70–100% semi-confluent monolayer of PMVECs. Amplification/expansion of primitive hematopoietic $CD34^+$ stem and progenitor cells in vitro increases significantly within 7 days when the $CD34^+$ stem and progenitor cells are directly cultured on endothelial cells. This is in contrast to the result occurring when $CD34^+$ stem and progenitor cells are cultured with endothelial cells in diffusion chambers preventing $CD34^+$ stem cell-to-endothelial cell interactions.

Utilizing PMVECs provides several advantages over other hematopoietic culture systems. For example, PMVEC is a homogeneous cell line in comparison to bone marrow stromal cell monolayers, a heterogeneous cell population containing endothelial cells, fibroblasts, adipocytes, macrophages and osteoclasts. These heterogeneous primary bone marrow stromal layer have been typically employed in previous hematopoietic culture systems. Thus, analysis of the mechanisms involved in hematopoiesis is significantly easier in the homogeneous PMVEC culture system than the heterogeneous bone marrow stromal culture system. In addition, the PMVEC cell line grows rapidly having a doubling rate of 48 hours, can be passed for as many as 6 months (or 54 passages), has minimal growth requirements and can be easily maintained under low serum culture conditions (1% FCS). In contrast, stromal cells have a limited passage capability.

In addition, the PMVEC cell culture system is able to support significant $CD34^+$ stem and progenitor cell amplification/expansion. For example, between days 7 and 14 of culture, this culture system shows significant $CD34^+$ stem and progenitor cells amplification/expansion. At day 7 an approximately 10 fold amplification/expansion of $CD34^+$ cells was measured and a greater than 95 fold amplification/expansion of $CD34^+$ cells was measured by day 14 of culture. By comparison, liquid cultures and stromal cell coculture systems typically yield a ≦3 fold amplification/expansion by day 7 and the percentage of $CD34^+$ cells rapidly decreases by 14 days of culture. The ability of the present method to significantly amplify/expand the number of CD34$^+$ CD38$^-$ stem cells, CFU-GM and non-adherent cells after 7 days of culture makes the culture system an attractive alternative to other short-term and long-term culture systems. The PMVEC cell culture system also has the advantage of supporting human, non-human primate and murine hematopoietic stem and progenitor cell proliferation. This makes it possible to study hematopoiesis in both humans and in animal models. In addition, both irradiated and formalin-fixed PMVEC monolayers can support hematopoietic progenitor cell amplification/expansion.

CD34$^+$ stem and progenitor cells are co-cultured with endothelial cells and are treated with cytokines in the present method. To promote amplification/expansion of the CD34$^+$ stem and progenitor cells, cytokines matched to the species of CD34$^+$ cells utilized are added to the CD34$^+$ cell-endothelial cell culture. While use of at least a single cytokine is required for CD34$^+$ cell amplification/expansion, combinations of cytokines can also be employed and are, in fact, preferred. Examples of suitable cytokine combinations for use in the amplification/expansion of human CD34$^+$ stem and progenitor cells include, but are not limited to, GM-CSF alone; GM-CSF+SCF; IL-3+SCF+IL-6 and GM-CSF+IL-3+SCF+IL-6. Preferably, the CD34$^+$ hematopoietic cell-endothelial cell culture is treated with GM-CSF+IL-3+SCF+IL-6. The amount of each cytokine used and the combination of cytokines selected will vary depending on several variables, but are readily determinable by those skilled in the art. For example, the CD34$^+$ hematopoietic stem cells-endothelial cells can be cultured with 0.1–20.0 ng/ml of GM-CSF, 1.0–200.0 ng/ml of IL-3, 5.0–500.0 ng/ml of SCF and/or 1.0–100.0 ng/ml of IL-6. Preferably, 2 ng/ml of GM-SCF+10 ng/ml of IL-3+100 ng/ml of SCF+10 ng/ml of IL-6 are used.

When highly purified CD34$^+$ stem and progenitor cells were cultured with combinations of either GM-CSF+SCF, IL-3+SCF+IL-6 or GM-CSF+IL-3+SCF+IL-6 in liquid suspension for the short-term (7 days), no amplification/expansion or maintenance of primitive CD34$^+$ cell number was detected, although the total number of non-adherent cells and CFC increased 10.2 and 2.9 fold, respectively in GM-CSF+IL-3+SCF+IL-6 treated cultures. These findings suggest that cytokines alone are not sufficient for the in vitro amplification/expansion of CD34$^+$ stem and progenitor cells on endothelial monolayers and that CD34$^+$ hematopoietic cell-to-PMVEC interactions, other soluble growth factors, membrane-bound growth factors, cellular adhesion molecules, or extracellular matrix proteins produced by cytokine activated endothelial cells may be involved. In addition, the endothelial cell-derived extracellular matrix may bind these growth factors and present these molecules in active form to the stem cell.

The mechanism by which the present culture system supports primitive CD34$^+$ hematopoietic stem and progenitor cell amplification/expansion is not clear. It is possible, however, that the cytokine-treated PMVEC produce a potentially novel hematopoietic growth factor(s) that supports primitive CD34$^+$ stem and progenitor amplification/expansion. Currently, the mechanism by which PMVEC monolayers support the amplification/expansion of primitive CD34$^+$ hematopoietic stem and progenitor cells in response to a combination of exogenous growth factors is being investigated.

Purified CD34$^+$ stem and progenitor cells from human bone marrow have been demonstrated to be capable of long-term and multilineage hematopoietic reconstitution. In bone marrow transplantation, committed progenitor cells, such as the CFU-GM, are required, along with pluripotent CD34$^+$ stem cells, in order for the recipient to withstand early aplasia and follow through to full hematopoietic reconstitution. An important breakthrough in clinical bone marrow transplantation is the application of the present culture system to a large-scale bioreactor using this culture system that supports the amplification/expansion of primitive CD34$^+$ hematopoietic stem and progenitor cells which contain progenitors capable of self-renewal, multilineage differentiation, and long-term hematopoiesis. Specifically, 1.5×10$^7$ CFU-GM progenitor cells can be generated from as few a 1–2×10$^6$ CD34$^+$ stem and progenitor cells within 14 days of culture. This is the number of CFU-GM required for engraftment of humans following autologous bone marrow transplantation. This number of CD34$^+$ stem and progenitor cells can routinely be obtained from one 15 ml bone marrow aspirate in a physician's office. Amplification/expansion of CD34$^+$ stem and cells in the present culture system will likely reduce the volume of marrow to be harvested, decrease the likelihood of general anesthesia, promote early recovery of hematopoiesis, ameliorate severe cytopenia, and promote shorter hospitalization and increased survival in personnel exposed to myelotoxic agents and/or radiation. Thus, the present culture method has obvious and significant impact not only for the therapy of oncologic diseases by bone marrow transplantation, but also for treatment of bone marrow failure syndromes and, potentially, for the use of gene transfer methods in somatic gene therapy.

Accordingly, the present invention also relates to a method of engrafting CD34$^+$ stem and progenitor cells in a patient. This method involves isolation of CD34$^+$ stem and progenitor cells and co-culturing the isolated CD34$^+$ stem and progenitor cells with endothelial cells in the presence of cytokines as discussed above. The method further requires the isolation of the amplified/expanded CD34$^+$ stem cells from the culture. (The present method can also be used on unseparated bone marrow rather than purified CD34$^+$ stem and progenitor cells.)

This present invention also relates to a method of engrafting more mature hematopoietic cells in a patient for short term hematopoietic support. This method involves the isolation and amplification/expansion of CD34$^+$ hematopoietic cells outlined in the preceding paragraph. This method does not require further isolation of CD34$^+$ stem and progenitor cells as the entire expanded population of CD34$^+$ cell and more differentiated hematopoietic cells (non CD34$^+$) are infused in the patient as outlined above. This can be done using methods well known in the art. Finally, the isolated amplified/expanded cells are infused into the patient using methods well known in the art.

Proliferating CD34$^+$ stem and progenitor cells in this culture (as well as more mature elements) may also be manipulated by gene insertion/gene therapy techniques before reengraftment into the patient. Thus, the present culture system could revolutionize gene therapy of stem cells, and provide a cure, for example, for sickle cell anemia.

The present technique can also be used in conjunction with "marrow purging" techniques to remove unwanted cells (i.e. tumor cells, T lymphocytes) before reinfusion into the patient. The culture conditions may also be manipulated to produce one specific blood cell type (such as platelets or red blood cells) to be reinfused/transfused back into patients. For example, autologous transfusion has great utility in cancer patients or in situations where the donor pool may be contaminated by an infectious agent.

Large-scale utilization of this culture system could be useful in amplifying/expanding primitive CD34$^+$ hematopoietic stem and progenitor cells and committed progenitor cells in vitro, permitting infusion of autologous cells or allogeneic cells into humans, for example, during drug-induced neutropenia or after bone marrow transplantation, as well as in gene therapy of hematopoietic CD34$^+$ stem and progenitor cells. It may be possible to employ the present culture system in known bioreactors to generate large quantities of CD34$^+$ stem and progenitor cells.

Having described the invention, the following examples are given to illustrate specific applications of the invention including the best mode now known to perform the invention. These specific examples are not intended to limit the scope of the invention described in this application.

EXAMPLES

Example 1

CD34$^+$ Bone Marrow Cells

Human vertebral body bone marrow was procured from cadavers. The procedure utilized to procure the bone marrow is described in the Naval Medical Research Institute publication no. 90-62 (("The Procuring and Processing of Human Cadaveric Bone Marrow", T. R. Faloon), available from the Defense Technical Information Center, AD# A226 538).

Briefly, marrow was obtained from the bone matrix by sterile technique and placed in sterile culture support media. Low density mononuclear cells were separated over Ficoll-Hypaque (specific gravity 1.077 g/ml; Pharmacia Fine Chemicals, Piscataway, N.J.) density gradients at 400 g for 30 min at 22° C. Low density cells at the interfaces were harvested, washed twice by centrifugation (400 g for 10 min) and resuspended in Iscove's Modified Dulbecco's Medium (IMDM, MA Bioproducts, Walkersville, Md.) supplemented with 10% heat-inactivated FBS (Hyclone, Logan, Utah), 100 mg/ml L-glutamine (Gibco, Grand IsLand, N.Y.), and 100 U/ml penicillin/streptomycin (Gibco, Grand IsLand, N.Y.). Unless otherwise noted this culture medium will be referred to as complete culture medium.

CD34$^+$ bone marrow stem and progenitor cells were further purified by positive immunomagnetic selection using a monoclonal antibody specific for the CD34 antigen (K6.1) as described in the Kessler patent application discussed above. The monoclonal antibody K6.1 was produced by fusing SP-2/0-AG14 plasmacytoma cells (American Type Culture Collection (ATCC), Rockville, Md.) with splenocytes from a BALB/cByJ mouse (Jackson Laboratory, Bar Harbor, Me.) which had been hyperimmunized with viable KG-1a cells (ATCC, Rockville, Md.). Injections containing 10 to 20 million KG-1a cells washed in saline were performed approximately monthly for a period of 6 months; the first and last immunizations were intravenous and the other immunizations were intraperitoneal. The last injection was performed 3 days prior to fusion. Cell hybridization and selection in HAT medium were performed according to the techniques of Kohler and Milstein (*Nature* 256:495, 1975), as modified by Fazekas de St. Groth and Scheldegger (*J. Immunol. Methods* 35:1, 1980), and Lane et al. (*J. Immunol. Methods* 72:71, 1984).

Culture supernatants collected approximately 2 weeks after fusion were screened for antibody activity against MY-10/CD34 antigen in KG-1a cell lysates by immunoblot ("Western blot") analysis. Initially, pools of about 10 growth positive hybridoma wells were screened, and individual wells of antibody positive pools were then screened. Antibody positive wells were subcloned by limiting dilution (Oi and Herzenberg, in *Selected Methods in Cellular Immunology*, (1980) Mishell and Shigii, eds., pp. 351–72), and clones were screened the same way.

KG-1a cells were solubilized at 1×10$^8$ cells/ml in Laemmli sample buffer (0.0625M Tris-HCl, pH 6.8; *Nature* 227:680, 1970), containing 0.5% Triton X-100 and 2 mM PMSF, and centrifuged (30,000×g, 30 min), and the supernatants were reduced in the presence of 50 mM DTT, 4% SDS, and 10% glycerol (60 min, 37° C.). Electrophoresis was performed on 8–16% pore-gradient, SDS polyacrylamide gels according to the method of Laemmli (*Nature* 227:680, 1970), as modified by Jones (in *Selected Methods in Cellular Immunology*, (1980) Mishell and Shigii, eds., pp. 398–440). Proteins were then transferred to nitrocellulose membranes for immunoblot analysis (Towbin et al., *Proc. Nat. Acad. Sci. USA* 76:4350, 1979, and Burnette, *Anal. Biochem.* 112:195, 1981), using alkaline phosphatase conjugated goat anti-mouse IgG antibody (BioRad Labs, Richmond, Calif.) for detection with BCIP/NBT as substrate (Kirkegaard & Perry Laboratories, Gaithersburg, Md.).

The hybridoma clone K6.1 was identified as producing a monoclonal antibody of the IgG2a isotype, as determined with an isotype screening ELISA kit (Zymed Laboratories, S. San Francisco, Calif.) on immobilized KG-1a cells (Cobbold and Waldmann, *J. Immunol. Methods* 44:125, 1981). The hybridoma was expanded in roller bottles in IMDM containing fetal calf serum (Hyclone). After supernatant harvesting, the K6.1 antibody was purified by hydroxylapatite chromatography (Stanker et al., *J. Immunol. Methods* 76:157, 1985), followed by pH-gradient elution from protein A-Sepharose (Ey et al., *Immunochemistry* 15:429, 1978). The yield of antibody was 40–45 µg/liter of supernatant. This was concentrated on ultrafiltration membranes (Amicon YM-10, Danvers, Mass.), and dialyzed into normal saline. Analysis of antibody purity was performed on 30–40 µg reduced and unreduced samples by SDS-polyacrylamide gel electrophoresis under Laemmli conditions, followed by Coomassie blue staining.

For positive immunoselection of CD34$^+$ cells, all cell washing, incubation and selection steps were performed at 4° C. (unless noted otherwise) in 0.2 µm sterile filtered "immunoselection washing buffer". The immunoselection washing buffer consisted of Hanks' balanced salt solution containing 12.5 mM HEPES buffer, 1000 units/ml DNAse 1 (Calbiochem), and 5% heat-inactivated pooled human AS serum (#34004-1, Pel-Freez Clinical Systems, Brown Deer, Wis.). The human serum was previously dialyzed extensively (40 volumes×5 changes) against PBS to remove traces of biotin. This was included as a source of human IgG to saturate Fc receptors and minimize cytophilic binding of the cell specific antibody (i.e., K6.1); for therapeutic immunoselection purposes, it was assumed that substitutes such as dialyzed serum from the marrow donor or pharmaceutically approved gamma globulins for injection would be used.

Bone marrow mononuclear cells were washed and adjusted to a concentration of 50×10$^6$/ml. Biotinylated-K6.1 antibody was prepared by mixing purified K6.1 with NaHCO$_3$ to give a solution containing 3 mg antibody/ml in 0.1M NaHCO$_3$. Biotin-N-hydroxysuccinimide ester (Calbiochem, La Jolla, Calif.) was dissolved in dimethylsulfoxide (DMSO) at a concentration of 12 mg/ml, and 5.0 µl of this was added to each ml of antibody solution. After 1 hr at room temperature, NH$_4$HCO$_3$ was added to 50 mM final concentration to stop the reaction. The mixture was then passed through a Sephadex PD-10 column (Pharmacia) equilibrated in phosphate-buffered saline (PBS, 6.7 mM Na phosphate, pH 7.2, 137 mM NaCl) to desalt and exchange the buffer. The biotinylated-K6.1 antibody was added at a ratio of 6–10 μg/ml of cell suspension and incubated with occasional mixing for 30 min at 4° C. The cells were then washed by centrifugation 3–4 times, and set to a concentration of $25 \times 10^6$/ml.

DYNABEADS M-450 (Dynal Incorporated, Great Neck, N.Y.) were activated with goat anti-biotin antibody. The number of DYNABEADS used was proportional to the total number of bone marrow mononuclear cells, using a ratio of 1 bead/10 cells. Anti-goat IgG DYNABEADS were washed magnetically 4–5 times with a rare-earth magnet. The beads were then suspended at a concentration of $1 \times 10^8$/ml in washing buffer containing 2.5 μg/ml affinity purified goat anti-mouse biotin antibody (#SP-3000, Vector Laboratories, Burlingame, Calif.), mixed vigorously for 30 min at room temperature, and then washed magnetically twice, and resuspended to $1 \times 10^8$/ml. This concentration of anti-biotin was optimized in preliminary titration studies using as an endpoint the kinetics of cell dissociation from the magnetic beads. The binding of anti-goat anti-biotin does not reach equilibrium under these conditions; varying the anti-biotin provided a convenient way to compensate indirectly for different cell surface antigen densities, by controlling the amount of biotin-anti-biotin crosslinking.

The bone marrow mononuclear cells, containing biotinylated-K6.1 antibody coated target cells, were incubated with the anti-biotin DYNABEADS for 30 min on a rotator (approx. 30 rpm). The magnetic $CD34^+$ stem and progenitor cells were then selected by attraction to a samarium-cobalt magnet, and removal of non-target cells free in suspension. These cells were purified by a further 4–5 washing cycles in which the magnet was removed, the cells resuspended, and the magnet reapposed, with removal of non-target cells free in suspension. Finally, the magnetic $CD34^+$ stem and progenitor cells were suspended in medium (e.g., IMDM) containing 2.5 mg/ml biotin, put on a rotator for 1–2 hr, and free $CD34^+$ cells were recovered from magnetically immobilized DYNABEADS. The magnetic separation can be accomplished using the magnetic separation device described in U.S. Pat. No. 4,710,472 issued 1 Dec. 1987 to Saur, Reynolds and Black.

Cells by this procedure showed >99% positive reactivity with a second CD34-specific monoclonal antibody, MY10 (HPCA-2) (Becton Dickinson Immunocytometry Systems, San Jose, Calif.), by flow cytometric analysis indicating that a highly purified population of cells expressing the CD34 surface membrane antigen was obtained which contained highly enriched hematopoietic stem cells, progenitor cells and essentially no mature blood cells.

Isolated $CD34^+$ bone stem and progenitor cells were cryopreserved ($1–5 \times 10^6$ cells/1 ml vial) and stored under liquid nitrogen prior to experimentation. Before use the $CD34^+$ stem and progenitor cells were thawed using standard techniques.

Processing of $CD34^+$ Cells for Culture

Cryopreserved $CD34^+$ stem and progenitor cells were thawed rapidly at 37° C., diluted in a 10× volume of prewarmed (37° C.) complete culture medium. The thawed $CD34^+$ bone marrow cells were washed twice in complete culture medium, and resuspended at $1 \times 10^6$ cells/ml. Cell viability was >99% as determined by trypan blue dye exclusion (Coligan et al., *Current Protocols in Immunology*, (1992), Greene Publishing and Wiley-Interscience, New York).

At the start of experimentation, a sample of $CD34^+$ stem and progenitor cells was cultured to determine the number and type of hematopoietic colony forming cells (CFC) using a methylcellulose colony forming assay (Meisenberg et al., *Blood* 79:2267, 1992). Briefly, purified $CD34^+$ bone marrow stem and progenitor cells and non-adherent hematopoietic cells from harvested cultures were cultured in 35 mm Lux suspension culture dishes (Miles Laboratories, Naperville, Ill.) using a modification of the technique previously described (Meisenberg et al., *Blood* 79:2267, 1992). One milliliter of culture consisted of $5–500 \times 10^2$ bone marrow cells, IMDM medium (Quality Biologicals, Rockville, Md.), 1% methylcellulose, 30% heat inactivated fetal calf serum (FCS), 2 U/ml tissue culture grade erythropoietin (Amgen, Thousand Oaks, Calif.), 2 ng/ml GM-CSF, 10 ng/ml IL-3 (R&D Systems, Minneapolis, Minn.) and 5% conditioned medium from the bladder carcinoma cell line 5637 (ATCC, Rockville, Md.). The conditioned medium from cell line 5637 was used as a source of colony stimulating activity. Cultures were incubated at 37° C. in a humidified atmosphere of 5% $CO_2$ in air. On day 14 of incubation, cultures were evaluated to determine the number of colonies (>50 cells) which had developed. At day 14, aggregates of hemoglobin containing cells were recognized as BFU-E; aggregates of granulocytes and/or macrophages and/or megakaryocytes as CFU-MIX; and aggregates containing only granulocytes and macrophages as CFU-GM.

Endothelial Cell Culture and Culture Conditions

Porcine brain microvascular endothelial cells (PMVEC) were isolated and grown as previously described (Robinson et al., *In Vitro Cell. Dev. Biol.* 26:169–180, 1990). The phenotypic and growth properties of these cells have been extensively characterized (Robinson et al., *In Vitro Cell. Dev. Biol.* 26:169–180, 1990 and Robinson et al., *Blood* 77:294–305, 1991).

Briefly, PMVECs were isolated from the brains of 4- to 6 month old Yucatan minipigs. The brains were collected aseptically, immersed in 10% povidone-iodine (Sherwood Pharmaceutical Co., Rahway, N.J.) for 2 min. and washed 5–6 times with Hank's balanced salt solution (HBSS) (Gibco, Grand Island, N.Y.) to remove the residual iodine. Gray matter of the cortices was aspirated through a Pasteur pipette, centrifuged for 10 min at 500 g (room temperature), resuspended in HBSS and homogenized in a 40 ml dounce homogenizer. The homogenate was centrifuged, resuspended and subsequently sieved through sterile nylon fabric of 149-, 76-, and 20 micron mesh size. The retained microvessels were resuspended in 6 ml HBSS and spun through discontinuous Ficoll-Paque gradients (33%–67% and 67%–75%) (Pharmacia Inc., Piscataway, N.J.). The pelleted microvessels were resuspended in 2 ml HBSS and 2 ml collagenase (1 mg/ml) (Worthington Biomedical, Freehold, N.J.) was added. After 2 minutes, the microvessels were washed with HBSS and plated in 16-mm well coated with fibronectin (Pierce Chemical, Rockport, Ill.) in M199 media (Quality Biological Inc., Gaithersburg, Md.) supplemented with 10% fetal calf serum, 500 micrograms/ml sodium heparin (Sigma Chemicals, St. Louis, Mo.), and 2–10 uL/ml retinal-derived growth factor (see Robinson et al, *In Vitro Cell. Dev. Biol.* 26:169–180, 1990). The cultures were then grown at 37° C. in air with 5% $CO_2$. After 7 days the cells were subcultured and subcloned. After subcloning, the PMVEC cell lines were grown in IMDM supplemented with 10% fetal calf serum, 100 mg/mL L-glutamine and 100 U/mL penicillin/streptomycin (complete culture medium).

PMVEC were fed twice weekly with complete medium. When confluent, PMVEC monolayers were washed with PBS, trypsinized (0.25 mg trypsin/ml, 5 mM EDTA, 37° C., 10 minutes, Sigma, St. Louis, Mo.) and subcultured either in a ratio of 1:5 in 75 cm$^2$ flasks or at a cellular concentration of $1\times10^5$ cells/well in gelatin-coated 6-well, tissue culture plates (Costar, Cambridge, Mass.) containing 3 ml of complete culture medium supplemented with an additional 10% FCS. After 48–72 hr, the adherent PMVEC monolayers (70–80% confluent) were washed twice with complete culture medium to remove non-adherent PMVEC and the culture medium was replaced with 5 ml of complete cell culture medium.

Cytochemical Staining

For the morphological analysis of cell populations, $10^5$ cells in 0.1 ml of medium were centrifuged for 7 min at 500 rpm onto microscope slides by using a Cytospin-2 (Shandon Instruments, Sewickley, Pa.) centrifuge. Air-dried cell preparations were fixed in absolute methanol and stained with Wright-Giemsa stain. Morphological differential cell counts were obtained by oil immersion microscopy. At least 200 cells per slide were analyzed.

Statistical Analysis

Criteria for significance ($P<0.05$) was performed using Student's t-test.

Proliferation of CD34$^+$ Bone Marrow Cells in Culture

To compare the capacity of liquid suspension cultures, noncontact PMVEC monolayer cultures and contact PMVEC monolayer cultures to support the growth of CD34$^+$ bone marrow stem and progenitor cells, purified CD34$^+$ cells ($1\times10^5$ cells/well) (>99.5% positive) were added to each well (5 ml final volume) of 6-well tissue culture plates (Costar, Cambridge, Mass.) containing no PMVEC monolayer (liquid cultures), confluent PMVEC monolayers (contact cultures) and to the upper chamber of a collagen treated Transwell insert (0.4 μm pore size, Costar, Cambridge, Mass.) placed on top of PMVEC monolayers (noncontact cultures).

Cultures were treated with optimal doses of GM-CSF, GM-CSF+SCF, IL-3+SCF+IL-6 and GM-CSF+IL-3+SCF+IL-6. In particular, the cytokines were used at the following concentrations: 2 ng/ml of GM-CSF; 10 ng/ml of IL-3; 100 ng/ml of SCF; and 10 ng/ml of IL-6. All cultures were maintained at 37° C. in a humidified atmosphere at 5% $CO_2$ in air. Recombinant human growth factors (purchased from R&D Systems, Minneapolis, Minn.) used to stimulate colony formation included IL-3, GM-CSF, IL-6 and SCF.

After various days of culture, non-adherent cells were gently removed from the endothelial cell monolayers, washed twice with complete culture medium, and manual hemacytometer cell counts were performed using trypan blue exclusion dye. FIG. 1 shows the number of non-adherent cells harvested per culture condition after 7 days of incubation. The results are expressed as mean number of non-adherent cell counted+1SD of quadruplicate cultures from six experiments. As can be seen, for each specific cytokine combination the fold increase in the harvested nonadherent cells was greatest in the cultures where CD34$^+$ stem and progenitor cells were grown in contact with the PMVEC monolayer, intermediate in the transwell/noncontact culture and the least in the liquid cultures.

Specifically, compared to CD34$^+$ bone marrow stem and progenitor cells grown in liquid culture, the number of harvested non-adherent cells was significantly greater (2.3–4.0 fold) in cultures grown in contact with PMVEC and stimulated with GM-CSF+SCF, IL-3+SCF+IL-6, or IL-3+GM-CSF+SCF+IL-6. In addition, the combination of GM-CSF+SCF+IL-6 was superior to GM-CSF+SCF or IL-3+SCF+IL-6 in each culture condition. There were 10.9, 18.9, and 39.6 fold increases in the number of non-adherent bone marrow cells harvested in contact PMVEC stimulated with GM-CSF+SCF, IL-3+SCF+IL-6, and GM-CSF+IL-3+SCF+IL-6, respectively. The least effective stimulus was the combination of GM-CSF+SCF, while the most effective stimulus was the combination of GM-CSF+IL-3+SCF+IL-6. The addition of IL-3+IL-6 increased the number of non-adherent cells by 3.6 fold. None of the cytokine combinations appeared to have any effect on the rate of development or the morphological organization of the adherent PMVEC monolayer.

Immunophenotype of Cultured Bone Marrow Cells

Figure 2:
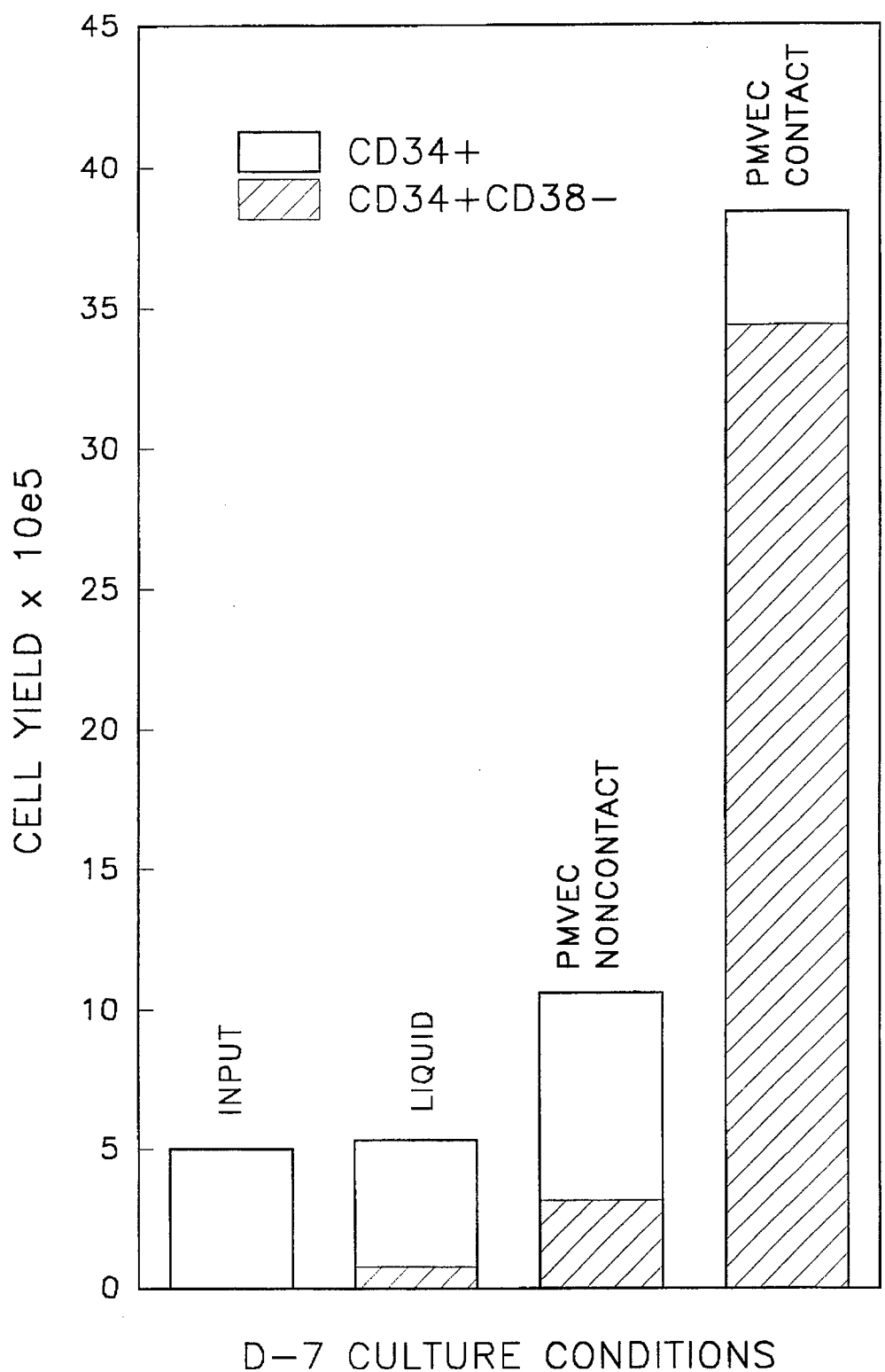
FIG. 2 shows the amplification/expansion of human CD34+ stem and progenitor cells after 7 days of culture in PMVEC treated with GM-CSF+IL-3+SCF+IL-6.

The effects of various cytokine combinations and culture conditions on the amplification/expansion proliferation and maturation of CD34$^+$ hematopoietic bone marrow stem and progenitor cells after 7 days of culture were assessed by measuring the expression of CD34 and CD38 cell surface antigens. The results on cells cultured for 7 days are shown in Table 1 and FIG. 2.

Simultaneous two-color cytometric analysis of cultured non-adherent cells was performed at day 7 of culture. Briefly, non-adherent cells removed from liquid cultures, contact endothelial cell cultures and noncontact endothelial cultures (upper compartment of the Transwell chamber) were harvested, washed twice in complete culture medium, and resuspended in PBS supplemented with 2% (wt/vol) bovine serum albumin (BSA) and 0.1% sodium azide (staining medium). Non-adherent cells were first incubated for 30 minutes with saturating concentrations of anti-CD34 antibody (K6.1 MAb). After two washes with staining medium, cells were incubated for an additional 30 minutes with biotinylated goat anti-mouse IgG2a. After a second series of two washes with staining medium, FITC-conjugated CD38 and APC-streptavidine were added together and incubated for an additional 30 minutes. Finally, cells were washed twice with staining medium and fixed with 1% paraformaldehyde. Each incubation step was done in the dark, at 4° C., and cells stained with the appropriate conjugated isotype antibodies were used as controls. At least 10,000 events were collected in listmode on a Coulter Elite (Coulter, Hialeah, Fla.) flow cytometer.

Figure 3:
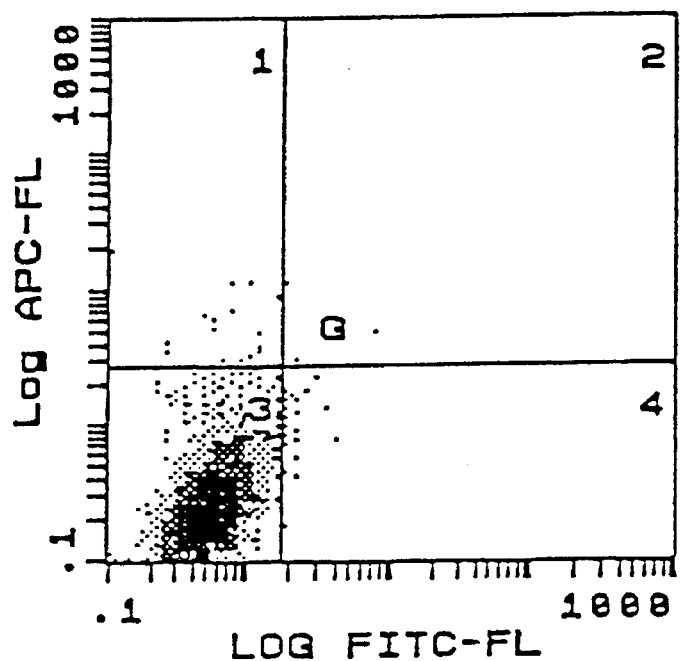
FIG. 3 shows the amplification/expansion of CD34+ bone marrow stem and progenitor cells on cytokine treated PMVEC monolayers. PMVEC monolayers were initiated with 5×10$^5$ purified CD34+ human bone marrow stem and progenitor cells and cultured for 7 days in the presence of GM-CSF (2 ng/ml)+IL-3 (100 ng/ml)+IL-6 (10 ng/ml). After 7 days of culture, nonadherent hematopoietic cells were harvested from the PMVEC monolayers and stained with APC-conjugated anti-CD34 and FITC-conjugated anti-CD38 monoclonal antibodies. Panel A illustrates isotype control of cells of nonadherent cells harvested displaying nonspecific FITC (x-axis) and APC (y-axis) fluorescences. Panel B illustrates the log fluorescence distribution of CD34+ stem and progenitor cells along the y-axis and CD38+ cells along the x-axis of day-7 cultured nonadherent hematopoietic bone marrow cells.
Figure 3:
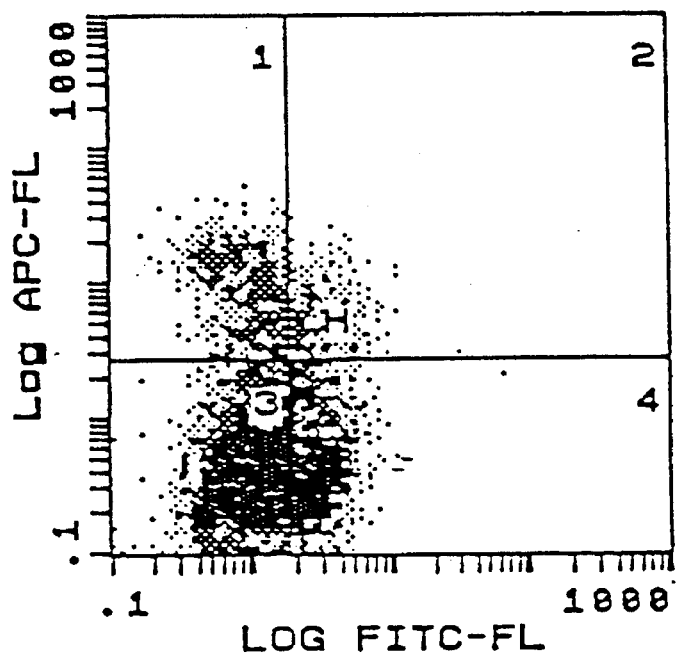

Neither unstimulated nor cytokine-treated PMVEC stained positive for anti-human CD34 and CD38 surface antigens. As shown in Table 1 below, the number of CD34$^+$ bone marrow cells in PMVEC contact cell cultures increased 1.5, 1.9 and 7.6 fold in the presence of GM-CSF+SCF, IL-3+SCF+IL-6, and GM-CSF+IL-3+SCF+IL-6, respectively. Moreover, 68–78% of these harvested CD34$^+$ stem and progenitor cells were also negative for the CD38 antigen. (See FIG. 2 and FIG. 3.)

In contrast to the results obtained using PMVEC contact cultures, a smaller degree of CD34$^+$ bone stem cell amplification/expansion was measured in noncontact PMVEC cultures, with greater than 67% of these cells expressing the CD34$^+$ CD38$^+$ phenotype.

In liquid suspension culture, input levels of CD34$^+$ bone marrow stem and progenitor cells were maintained only with GM-CSF+IL-3+SCF+IL-6 (1.2 fold increase) cytokine treatment, however greater than 85% of these cells co-expressed the CD38 hematopoietic differentiation antigen.

$1.1\times10^4$ BFU-E, $1.8\times10^4$ CFU-BLAST, and $2.2\times10^4$ CFU-MK. The total number of colony forming cells (CFC) generated after 7 days in liquid suspension culture decreased

TABLE 1

Proliferation of primitive hematopoietic progenitor cells (CD34$^+$ CD38$^-$) in cytokine treated PMVEC cultures.

| Culture Conditions and Factors | Number of cell harvested × $10^5$/5 × $10^5$ CD34$^+$ cells cultured | | | | |
|---|---|---|---|---|---|
| | Cell Yield × $10^5$ | CD34$^+$ | CD38$^+$ | CD34$^+$ CD38$^-$ | CD34$^+$ CD38$^+$ |
| Input | 5.0 | 4.9 ± 0.1 | 4.2 ± 0.4 | 0.7 ± 0.5 | 4.2 ± 0.4 |
| Liquid Culture | | | | | |
| GM-CSF + SCF | 20.2 ± 4.7 | 2.5 ± 1.0 | 14.3 ± 1.7 | 0.5 ± 0.2 | 2.0 ± 0.8 |
| IL-3 + SCF + IL-6 | 32.4 ± 2.1 | 3.5 ± 2.1 | 25.7 ± 6.2 | 0.8 ± 0.5 | 2.7 ± 1.5 |
| GM-CSF + IL-3 + SCF + IL-6 | 56.1 ± 16.2 | 6.0 ± 3.1 | 49.1 ± 16.9 | 0.9 ± 0.8 | 5.1 ± 2.4 |
| PMVEC noncontact culture | | | | | |
| GM-CSF + SCF | 55.2 ± 1.0 | 8.8 ± 3.5 | 33.2 ± 3.9 | 2.8 ± 1.5 | 5.9 ± 2.6 |
| IL-3 + SCF + IL-6 | 79.3 ± 11.4 | 10.9 ± 5.7 | 60.3 ± 7.1 | 2.9 ± 1.5 | 7.9 ± 4.2 |
| GM-CSF + IL-3 + SCF + IL-6 | 87.1 ± 2.7 | 11.8 ± 7.3 | 64.6 ± 11.6 | 3.5 ± 2.4 | 8.3 ± 4.9 |
| PMVEC contact culture | | | | | |
| GM-CSF + SCF | 56.7 ± 11.0 | 7.3 ± 1.3 | 13.3 ± 2.2 | 5.7 ± 0.9 | 2.4 ± 0.4 |
| IL-3 + SCF + IL-6 | 94.4 ± 31.1 | 9.3 ± 4.7 | 22.3 ± 11.9 | 7.0 ± 2.8 | 2.3 ± 1.1 |
| GM-CSF + IL-3 + SCF + IL-6 | 210.2 ± 120.0 | 37.2 ± 18.5 | 56.2 ± 13.1 | 25.1 ± 10.8 | 12.1 ± 7.04 |

$5 \times 10^5$ CD34$^+$ bone marrow stem and progenitor cells were plated per culture treatment. Nonadherent cells were harvested on day 7 of culture. Cells of each culture were stained for phenotypic analysis with APC-conjugated anti-CD34 antibody (K6.1 MAb) and FITC-conjugated CD38. Stained cells were analyzed using two-color flow cytometry. The number of positive cells was corrected to reflect the total number of cells harvested/culture. Each point represent the mean number of positive cells from three different experiments.

Hematopoietic Colony Formation Potential of Non-Adherent Cells Harvested From Day 7 Cultures The growth of hematopoietic progenitor cells from day 7 non-adherent cells harvested from cytokine treated liquid suspension cultures, noncontact PMVEC monolayer cultures and contact PMVEC monolayer cultures was also investigated. The data in Table 2, shown below, indicate the total number of CFC, CFU-GM, CFU-MIX, CFU-BLAST, CFU-MK and BFU-E recovered per culture treatment. Cultures were initiated with 5×10$^5$ CD34$^+$ stem and progenitor cells containing 5.5×10$^4$ CFU-GM, 2.8×10$^4$ CFU-MIX, 25% in GM-CSF+SCF treated cultures, increased 1.5 fold in IL-3+SCF+IL-6 treated cultures and increased 3.2 fold in the presence of GM-CSF+IL-3+SCF+IL-6. In contrast, total clonogenic cell content expanded 3.3, 4.4, and 8.9 fold in PMVEC noncontact cultures and 10.5, 20.3, and 37.4 fold in PMVEC contact cultures treated with GM-CSF+SCF, IL-3+SCF+IL-6, and GM-CSF+IL-3+SCF+IL-6, respectively. Maximal increases in total non-adherent cells (42.0 fold), CFU-GM (33.3 fold), CFU-MIX (31.0 fold), BFU-E (50.2 fold), CFU-BLAST (33.6 fold) and CFU-MK (9.2 fold) were obtained with GM-CSF+IL-3+SCF+IL-6 treated PMVEC contact cultures, indicating the importance of direct cell-to-cell contact.

TABLE 2

Effect of various hematopoietic factor combinations on progenitor cell production from CD34$^+$ bone marrow cells cultured for seven days in liquid suspension culture, noncontact PMVEC culture and contact PMVEC culture.

| Culture Conditions and Factors | Number of colony forming cell × $10^4$ per culture | | | | | | |
|---|---|---|---|---|---|---|---|
| | Cell Yield × $10^5$ | CFU-GM | CFU-GEMM | BFU-E | CFU-BLAST | CFU-MK | Total |
| Input | 5.0 | 5.5 | 2.8 | 1.1 | 1.8 | 2.2 | 11.2 |
| Liquid Culture | | | | | | | |
| GM-CSF + SCF | 20.2 ± 4.7 | 4.5 ± 3.2 | 2.4 ± 0.7 | 0.6 ± 0.4 | 0.6 ± 0.2 | 0.1 ± 0.1 | 8.4 ± 2.7 |
| IL-3 + SCF + IL-6 | 32.4 ± 2.1 | 9.8 ± 4.6 | 4.3 ± 2.4 | 1.1 ± 0.4 | 1.3 ± 1.3 | 0.4 ± 0.3 | 17.1 ± 8.1 |
| GM-CSF + IL-3 + SCF + IL-6 | 56.1 ± 16.2 | 19.2 ± 7.9 | 9.1 ± 2.9 | 3.1 ± 1.2 | 3.7 ± 1.9 | 1.2 ± 0.6 | 36.5 ± 13.7 |

TABLE 2-continued

Effect of various hematopoietic factor combinations on progenitor cell
production from CD34+ bone marrow cells cultured for seven days in liquid
suspension culture, noncontact PMVEC culture and contact PMVEC culture.

| Culture Conditions and Factors | Cell Yield × 10⁵ | CFU-GM | CFU-GEMM | BFU-E | CFU-BLAST | CFU-MK | Total |
|---|---|---|---|---|---|---|---|
| PMVEC noncontact culture | | | | | | | |
| GM-CSF + SCF | 55.2 ± 1.0 | 5.6 ± 2.7 | 8.1 ± 1.3 | 3.4 ± 1.1 | 5.1 ± 3.1 | 1.5 ± 0.3 | 37.3 ± 13.9 |
| IL-3 + SCF + IL-6 | 79.3 ± 11.4 | 25.2 ± 17.9 | 6.2 ± 5.5 | 7.4 ± 4.2 | 6.7 ± 4.9 | 1.9 ± 0.8 | 49.7 ± 35.7 |
| GM-CSF + IL-3 + SCF + IL-6 | 87.1 ± 2.7 | 60.6 ± 39.8 | 12.3 ± 7.1 | 8.2 ± 4.7 | 16.2 ± 11.8 | 2.6 ± 0.6 | 100.1 ± 64.1 |
| PMVEC contact culture | | | | | | | |
| GM-CSF + SCF | 56.7 ± 11.0 | 60.1 ± 39.9 | 22.8 ± 12.1 | 9.3 ± 5.2 | 16.5 ± 9.2 | 3.8 ± 1.8 | 117.2 ± 73.3 |
| IL-3 + SCF + IL-6 | 94.4 ± 31.1 | 125.9 ± 107.3 | 35.6 ± 29.4 | 22.2 ± 16.2 | 38.2 ± 25.6 | 5.2 ± 3.5 | 228.3 ± 182.7 |
| GM-CSF + IL-3 + SCF + IL-6 | 210.2 ± 120.0 | 182.9 ± 56.6 | 86.8 ± 56.6 | 55.3 ± 30.8 | 60.6 ± 18.6 | 20.2 ± 9.1 | 418.8 ± 223.5 |

$5 \times 10^5$ CD34+ bone to marrow stem and progenitor cells were plated per culture treatment. Nonadherent cells were harvested on day 7 of culture. Nonadherent cells (5–500 × 10²) were cultured in 35-mm tissue culture dishes containing IMDM medium, 1% methylcellulose, 30% FCS, 2 U/ml tissue culture grade erythropoietin, 2 ng/ml GM-CSF, 10 ng/ml IL-3 and 5% conditioned medium from the bladder carcinoma cell line 5637 as a source of colony stimulating ac tivity. The number of myeloid and erythroid colonies were counted after 14 days of culture, and based on the total number of viable cells per culture the number of colonies was corrected to reflect the total number of CFC per culture condition. Values represent the number of colonies of triplicate cultures from three different experiments.

Example 2

Long-Term Growth Potential of Bone Marrow CD34+ Hematopoietic Stem and Progenitor Cells on Cytokine Treated PMVEC Monolayers Purified CD34+ human bone marrow stem and progenitor cells (5×10⁵ cells/flask) were inoculated in 75 cm² flasks containing PMVEC confluent monolayers, and 15 ml of complete culture medium supplemented with GM-CSF (2 ng/ml), IL-3 (10 ng/ml), SCF (100 ng/ml) and IL-6 (10 ng/ml). All cultures were maintained at 37° C. in a humidified atmosphere at 5% $CO_2$ in air. After 7 days, and subsequently at weekly intervals, all non-adherent cells were removed and counted (see FIG. 4), and 2×10⁶ non-adherent cells were reseeded onto fresh PMVEC monolayer cultures containing fresh medium supplemented with growth factors. Non-adherent cells were immunophenotyped for CD34 and CD38 cell surface antigens and assayed in methylcellulose to determine their clonogenic cell content (see FIGS. 4, 5 and 6).

Figure 4:
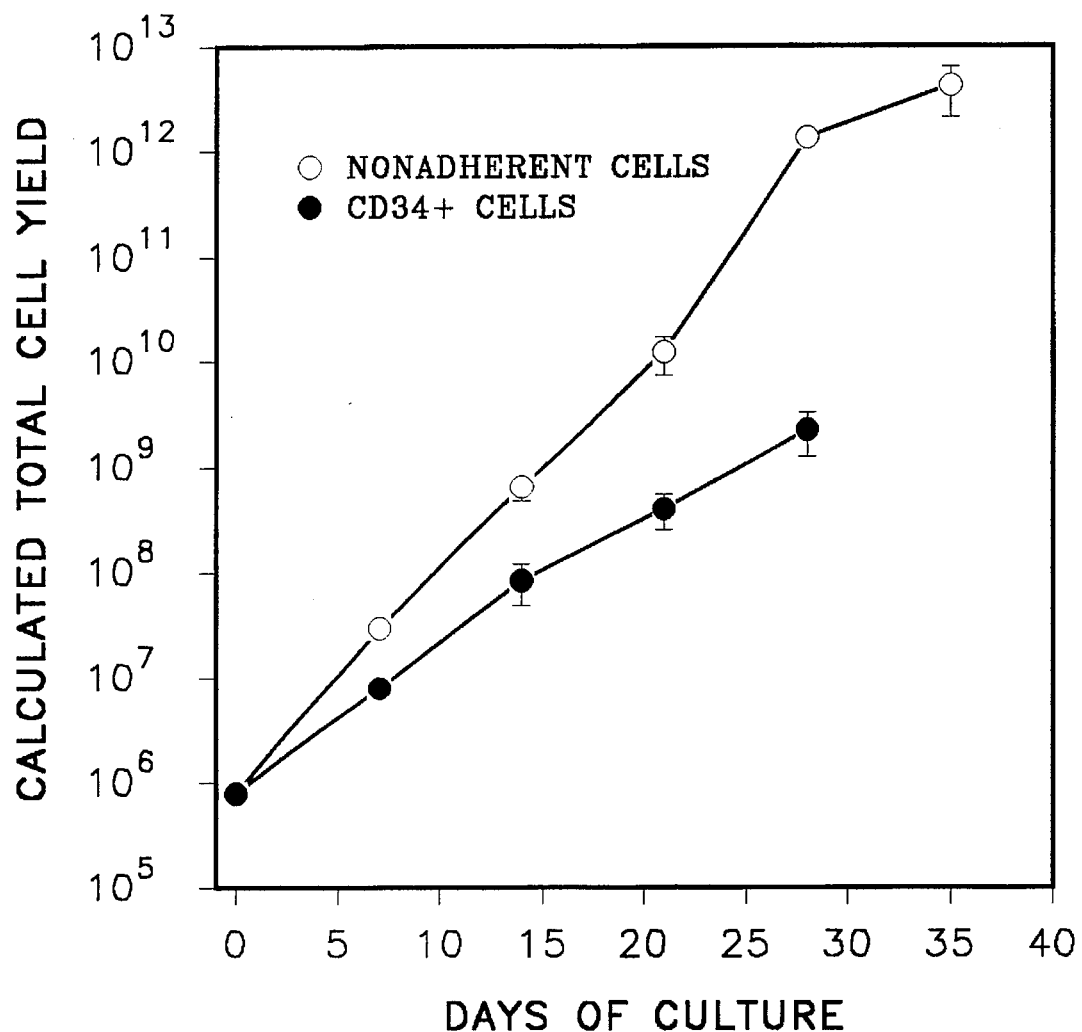
FIG. 4 shows the number of human nonadherent cells and CD34+ cells present in the PMVEC culture system at various stages of culture.
Figure 5:
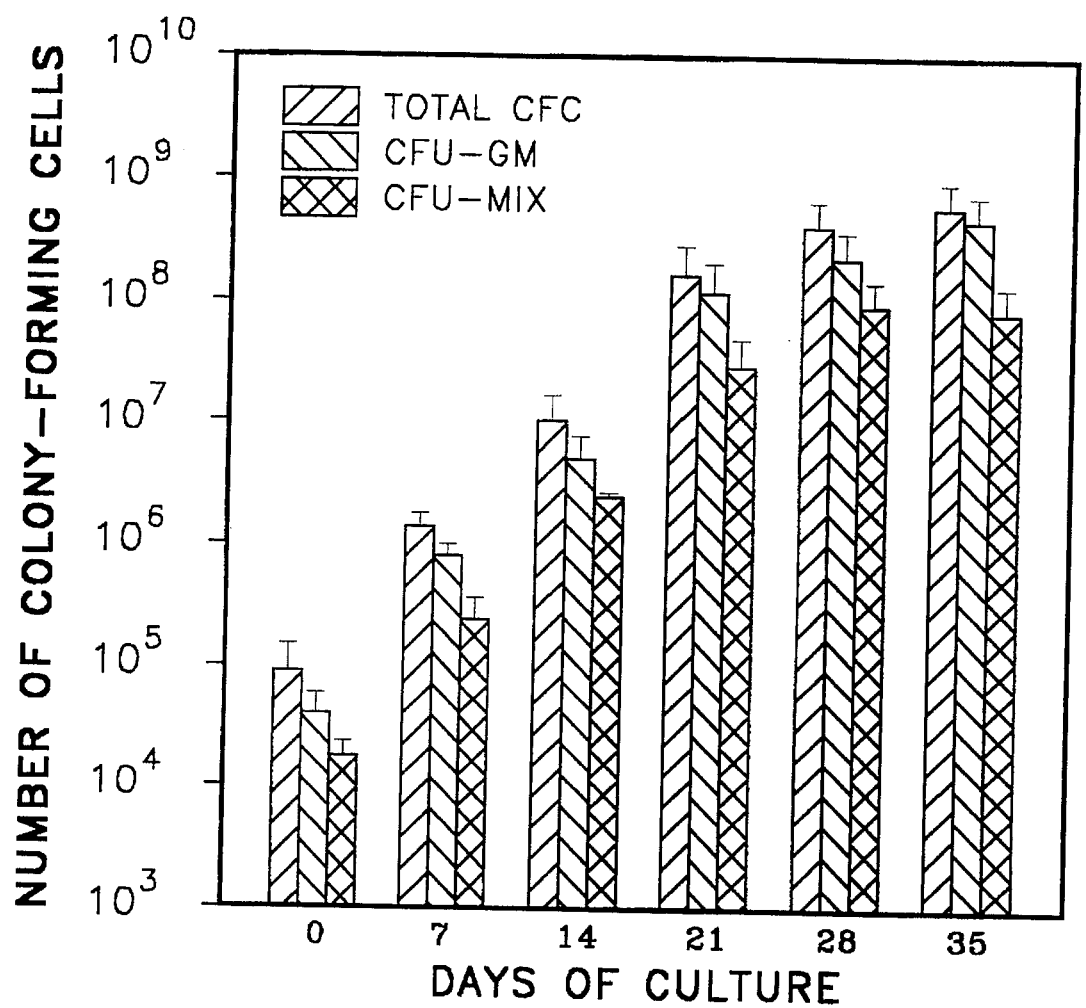
FIG. 5 shows the number of human colony forming cells (CFC) present in the PMVEC cultures at various stages of culture.
Figure 6:
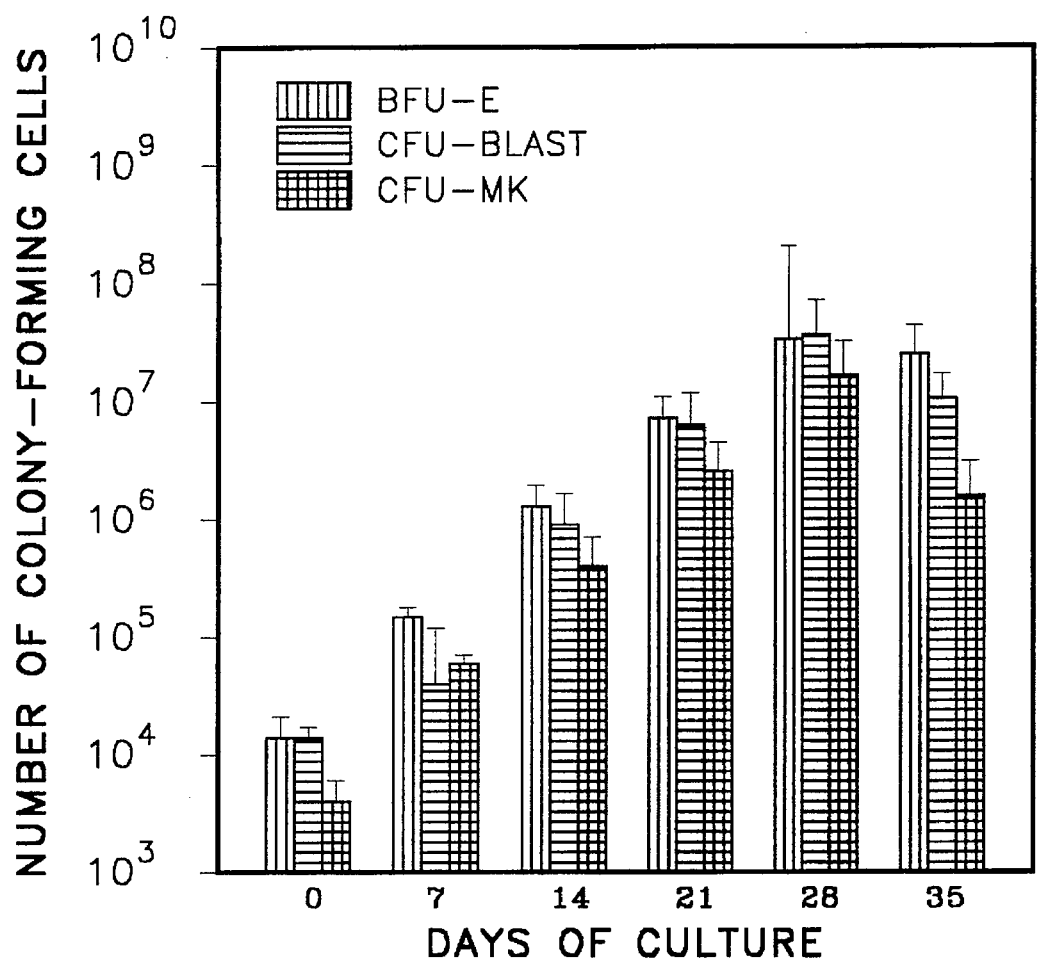
FIG. 6 shows the number of human colony forming cells (CFC) present in the PMVEC cultures at various stages of culture.

The effects of optimal concentrations of GM-CSF+IL-3+SCF+IL-6 on the growth of CD34+ hematopoietic stem and progenitor cells in long-term culture are shown in FIGS. 4, 5 and 6. At all sampling intervals, the cell viability of harvested non-adherent cells, as determined by trypan blue exclusion, was >95%. The number of non-adherent cells and CFC progenitors increased dramatically during the 35 day culture period. Non-adherent cell production peaked at day 35 with more than a calculated 5.31×10⁵ fold increase in cell number.

Furthermore, a 4510, 5677, 5177, 2607, 2407, and 4150 fold increase in the number of total clonogenic cells, CFU-GM, CFU-mix, CFU-BLAST, BFU-E and CFU-MK was detected in culture at day 28. Although the percentage of cells in culture that expressed the CD34+ surface antigen at days 7, 14, 21, and 28 decreased to 26.6%, 13.0%, 3.3% and 1.7%, respectively, the calculated absolute number of CD34+ stem and progenitor cells generated in this culture system increased 10.0, 105, 498, and 2854 fold over the same time interval. The presence of CD34+ stem and progenitor cells was <1% by day 35 and correlated with a significant decline in the number of assayable CFU-MIX, CFU-MK, CFU-BLAST and BFU-E; however, no significant changes in the number of CFU-GM were observed in comparison to day 28 values. In addition, the incidence of cells expressing either the CD15 or CD11b surface antigens increased rapidly with loss of CD34 antigen expression, with 14.8%, 42.4%, 43.4%, and 64.9% of the cells CD15+ and 44%, 43%, 59% and 66% of the cells CD11b+ at day 14, 21, 28, and 35 of culture, respectively. The immunophenotypically observed myeloid differentiation patterns were confirmed by cytological analysis of the harvested cells at the various time intervals.

Example 3

Murine Transplantation

Female mice (C57BL/6) were purchased from The Jackson Laboratory, Bar Harbor, Me., and housed 5 to 10 mice per cage. Animals were maintained on a 12-h light/dark cycle and were allowed food (Wayne Roden Blox) and water ad libitum. Mice 12–14 weeks old were used for these studies. Research was conducted according to the principles enunciated in the "Guide for the Care and Use of Laboratory Animals" prepared by the Institute of Laboratory Animal Resources, National Research Council.

Endothelial Cell Culture Conditions

Porcine brain microvascular endothelial cells (PMEVC) were grown as described above. Cells from actively growing monolayers (passages 8–21) were plated at a cellular concentration of 3×10⁴ cells/well in gelatin-coated 24-well, tissue culture plates containing medium QBSF-56 (Quality Biologicals, Gaithersburg, Md.) supplemented with 20% FBS (Hyclone, Ogden, Utah). After 24–48 hr, the culture medium was replaced with a low serum defined medium consisting of QBSF-56 (Quality Biologicals, Gaithersburg, Md.), supplemented with 1% heat inactivated FBS, 100 µg/ml L-glutamine and 1% penicillin/streptomycin.

Expansion of Bone Marrow Cells In Vitro

Ficoll-hypaque separated mononuclear bone marrow cells from the femora of mice ($5\times10^3$/well) were added with recombinant murine GM-CSF (5 ng/ml) and IL-3 (5 ng/ml) to each well of a 24-well culture plate (2 ml/well final volume) and incubated at 37° C. in a humidified 5% $CO_2$ in air atmosphere. After 7 days of incubation, pooled cells from blast colonies were dispersed from the endothelial monolayer with culture medium using a sterile 5 ml pipet. Blast cells were concentrated by centrifugation and resuspended in a solution of PBS supplemented with 1% FCS and 100 µg/ml penicillin/streptomycin.

Cell Suspensions

Mice were sacrificed by cervical dislocation, and the femurs and spleens were excised. Cells were flushed from the femurs with 5 ml of PBS containing 10% heat-inactivated fetal bovine serum (Hyclone, Logan, Utah) and dispersed throught a 25-gauge needle until a single-cell suspension was obtained. Spleens were pressed through stainless-steel mesh screens, and the cells were washed from the screens with 5 ml of medium. Cell concentrations and cellular viability were determined by manual hemacytometer counts via trypan blue dye exclusion.

Peripheral Blood Cell Counts

Peripheral blood was obtained from metaphane-anesthetized mice by cardiac puncture using heparinized syringes fitted with 22-gauge needles. White blood cell, red blood cell, and platelet counts were enumerated using a Baker Hematology 9000 Series Cell Counter System (Baker, Allentown, Pa.). In addition, blood smears were prepared and stained with Diff-Quick (Bayer Healthcare Corp, McGaw Park, Ill.). Morphological WBC differential cell counts were obtained by oil immersion microscopy. At least 20 cells per slide were analyzed.

Granulocyte-Macrophage Colony-Forming Cell (GM-CFC) Assay

Bone marrow and splenic CFU-GM were assayed in 35 mm Lux dishes (Miles laboratory, Naperville, Ill.) using a modification of the technique as previously described (Meisenberg et al, *Blood* 79:2267, 1992). One milliliter of culture consisted of $5-50\times10^4$ cells, Iscove's MEM (GIBCO, Grand Island N.Y.), 1% methylcellulose, 30% heat inactivated fetal calf serum (FCS), 5 ng/ml rmGM-CSF, and 5 ng/ml rmIL-3 (Genzyme, Boston Mass.). Cultures were incubated at 37° C. in a humidified atmosphere of 5% $CO_2$ in air. On day 14 of incubation, the number granulocyte-macrophage colony forming cell (CFU-GM) were determined in situ.

Statistical Analysis

Two-tailed Student's t-test was used to test for statistical difference. Significance level was set at $p<0.05$.

Survival of Mice Transplanted With Cells From Blast Colonies Grown on Endothelial Cells in the Presence of GM-CSF Mice were exposed bilaterally to gamma radiation at a dose rate of 1.0 Gy/min from a cesium-137 radiation source and on the following day infused from the tail vein with either saline, $5\times10^4$ nonadherent cells from liquid suspension cultures treated GM-CSF+IL-3 or $5\times10^4$ pooled blast cells from day 7 blast cell colonies grown on GM-CSF treated endothelial monolayers. Mice receiving a total dose of 10.0 Gy irradiation and either saline (control) or $5\times10^4$ nonadherent cells from day-7 GM-CSF+IL-3 liquid suspension cultures died in an average of $14\pm3$ days.

Peripheral blood was obtained from metaphane-anesthetized mice by cardiac puncture using heparinized syringes fitted with 22-gauge needles. White blood cell, red blood cell, and platelet counts were enumerated using a Baker Hematology 9000 Series Cell Counter System (Baker, Allantown, Pa.). In addition, blood smears were prepared and stained with Diff-Quick (Bayer Healthcare Corp, McGaw Park, Ill.). Morphological WBC differential cell counts were obtained by oil immersion microscopy. At least 200 cells per slide were analyzed. The number of white blood cell (WBC) and platlets reached a nadir by 4 days after irradiation and did not recover before the death of the animals. However, lethally irradiated mice receiving bone marrow transplants of $5\times10^4$ pooled blast cells from day 7 colonies grown on endothelial monolayers in the presence of GM-CSF+IL-3 all survived >60 days after transplantation.

Hematopoietic Recovery in the Bone Marrow and Spleen

Figure 7:
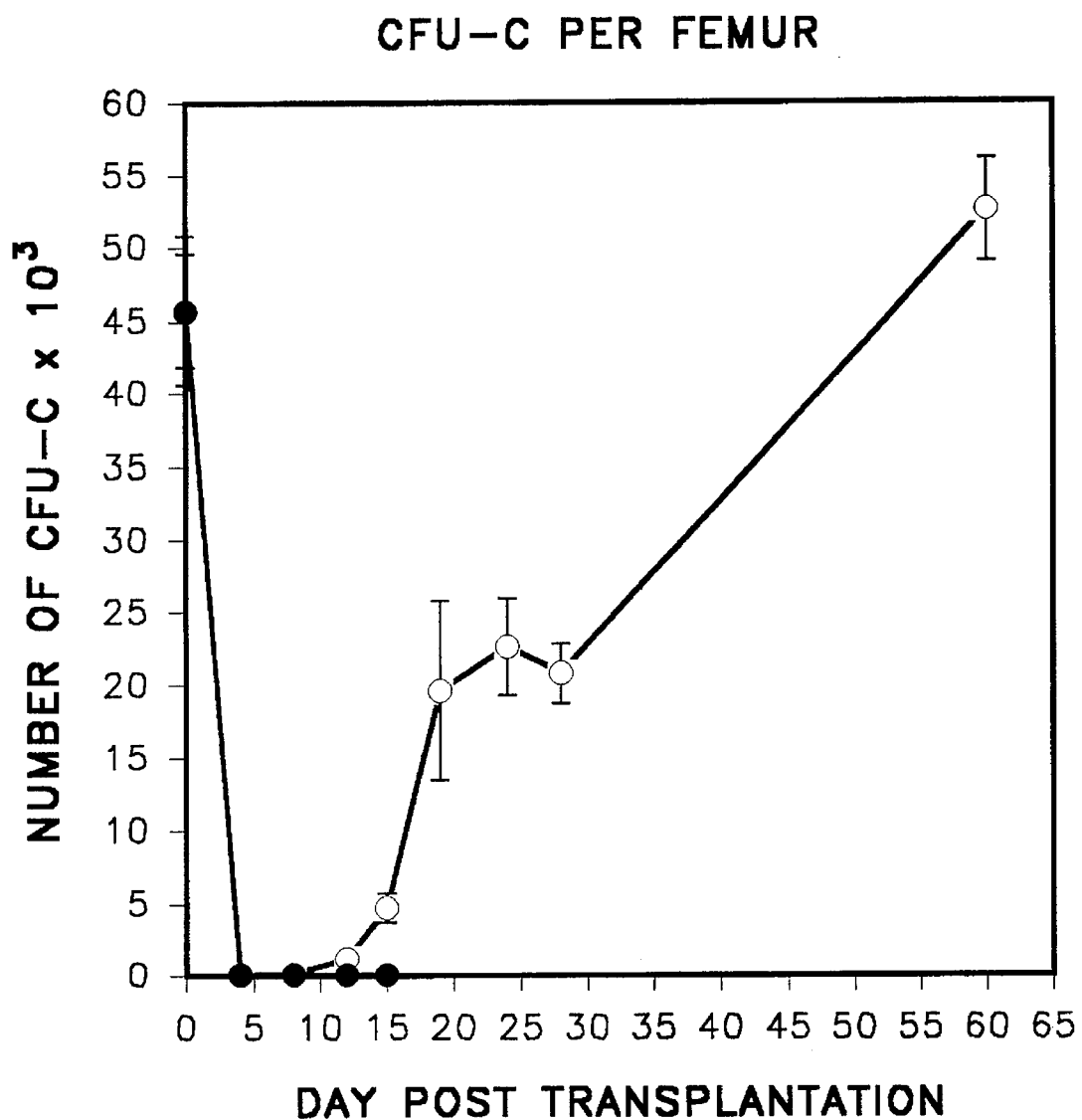
FIG. 7 shows changes in the number of murine CFU-GM per mouse femur. Mice were exposed to 10.0 Gy of irradiation and administered either $5\times10^4$ bone marrow MNC cells from day-7 liquid suspension cultures treated with GM-CSF+IL-3 (■), or $5\times10^4$ pooled blast cells from day-7 blast cell colonies grown on PMVEC monolayers in the presence of GM-CSF+IL-3(●). Each point represents the mean±SE of 8 mice from two separate experiments.
Figure 8:
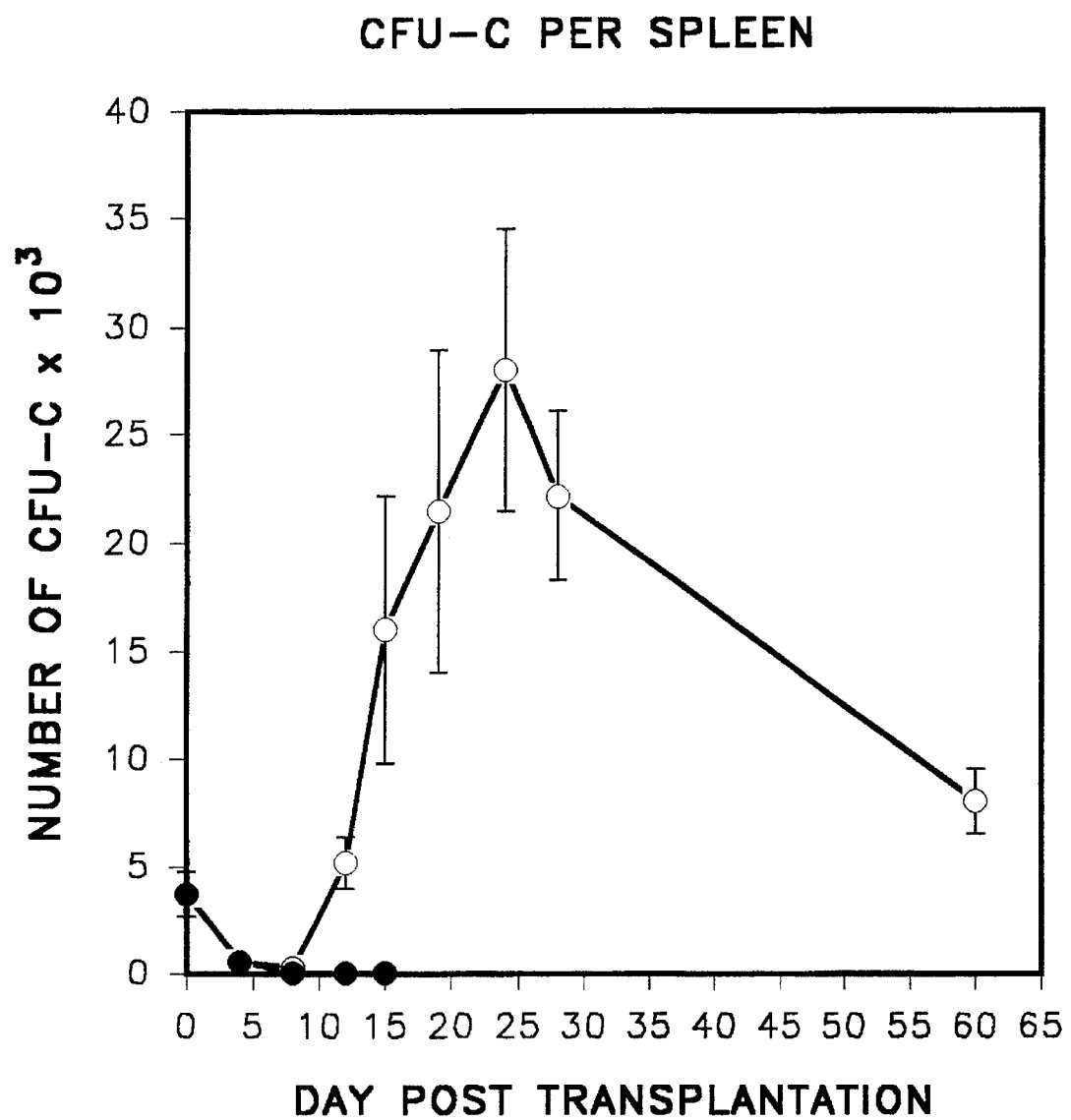
FIG. 8 shows changes in the number of murine CFU-GM per mouse spleen. Mice were exposed to 10.0 Gy of irradiation and administered either $5\times10^4$ bone marrow MNC cells from day-7 liquid suspension cultures treated with GM-CSF+IL-3(■), or $5\times10^4$ pooled blast cells colonies grown on PMVEC monolayers in the presence of GM-CSF+IL-3 (●). Each point represents the mean±SE of 8 mice from two separate experiments.

The total number of GM-CFC per femur and spleen were assayed at days 0, 4, 8, 12, 15, 19, 24, 28, and 60 following a lethal 10.0-Gy radiation exposure and bone marrow transplantation (FIGS. 7 and 8). Pooled blast cells harvested from GM-CSF+IL-3 treated PMVEC monolayers induced multilineage hematopoiesis as evidenced by changes in splenic and bone marrow stem and progenitor cell contents. The bone marrow cellularity of transplanted mice was reduced to $5.6\times10^5$ cell per femur (approximately 10% of normal bone marrow cellularity) 24 h after irradiation. The lowest splenic GM-CFC numbers were observed at 4 days following irradiation; splenic recovery occurred approximately 2 weeks post transplantation, with progenitor cell number overshooting control day-0 values before normalizing. Bone marrow stem cells and progenitor cells decreased four days after transplantation, and from day 12 increased gradually. However, they did recover to a normal level by day 60 post transplantation.

Hematopoietic Recovery in the Peripheral Blood

Figure 9A:
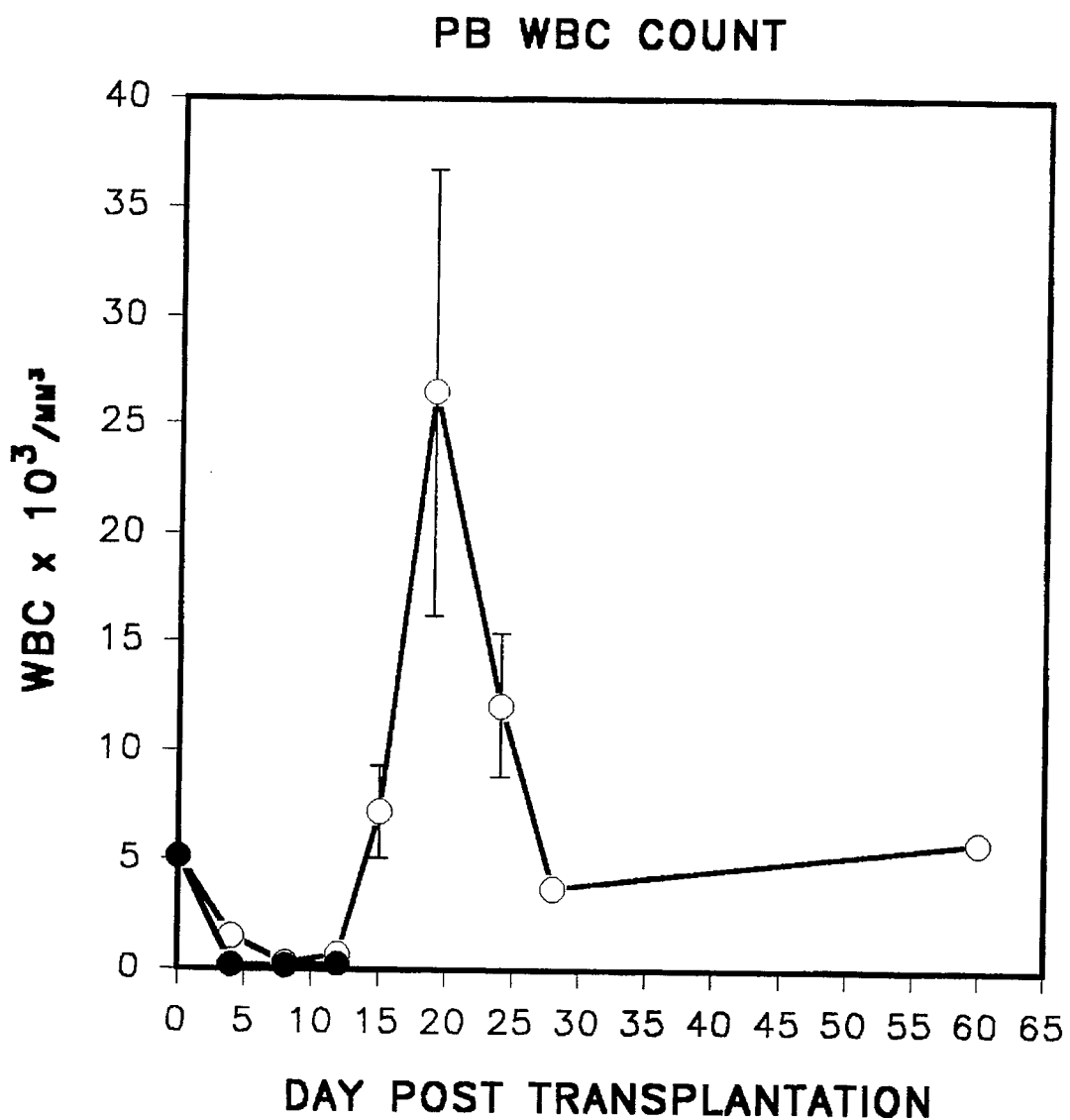
FIG. 9A shows the recovery of murine peripheral blood white blood cell numbers.
Figure 9B:
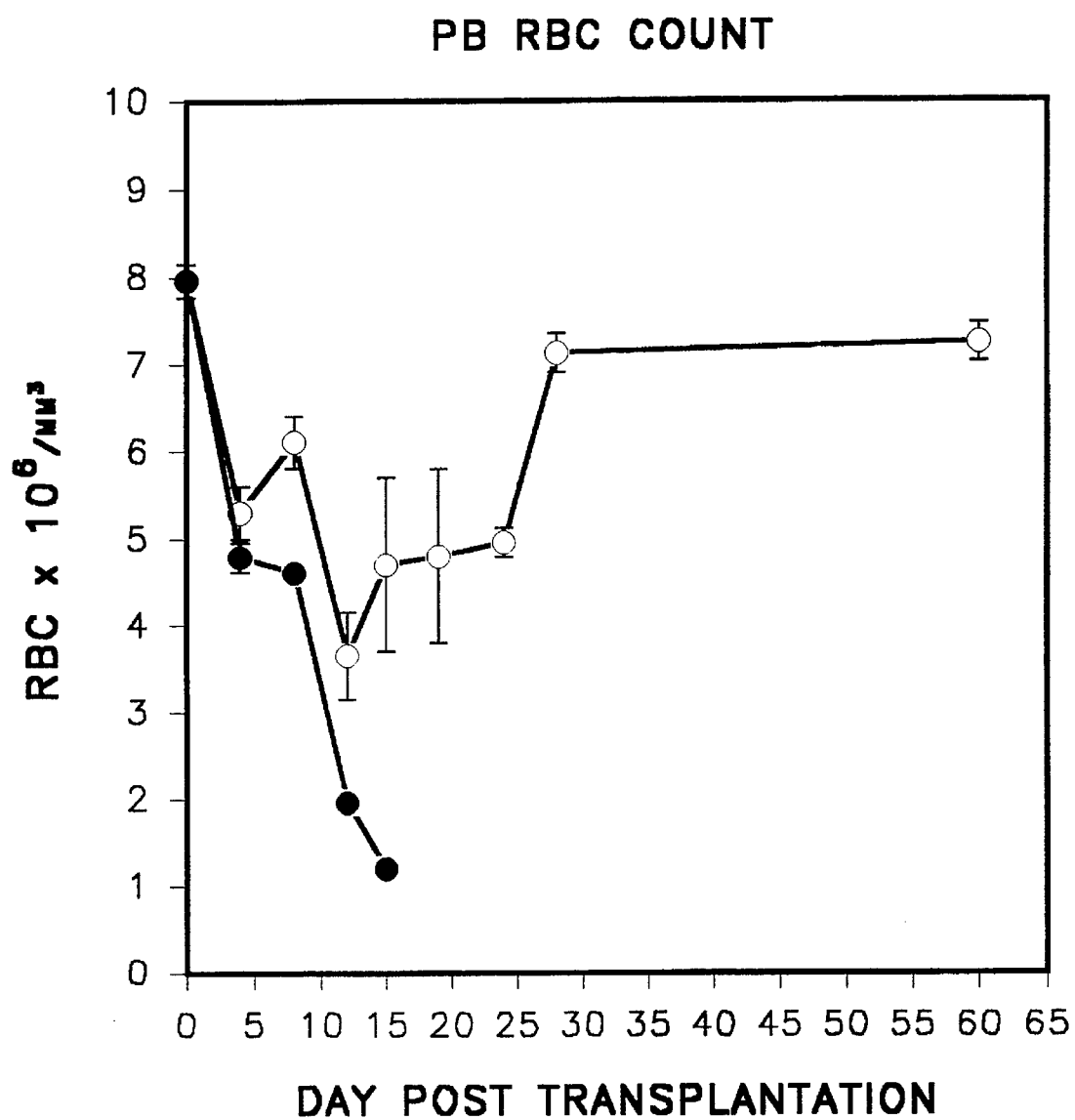
FIG. 9B shows the recovery of murine peripheral blood red blood cell numbers.
Figure 9C:
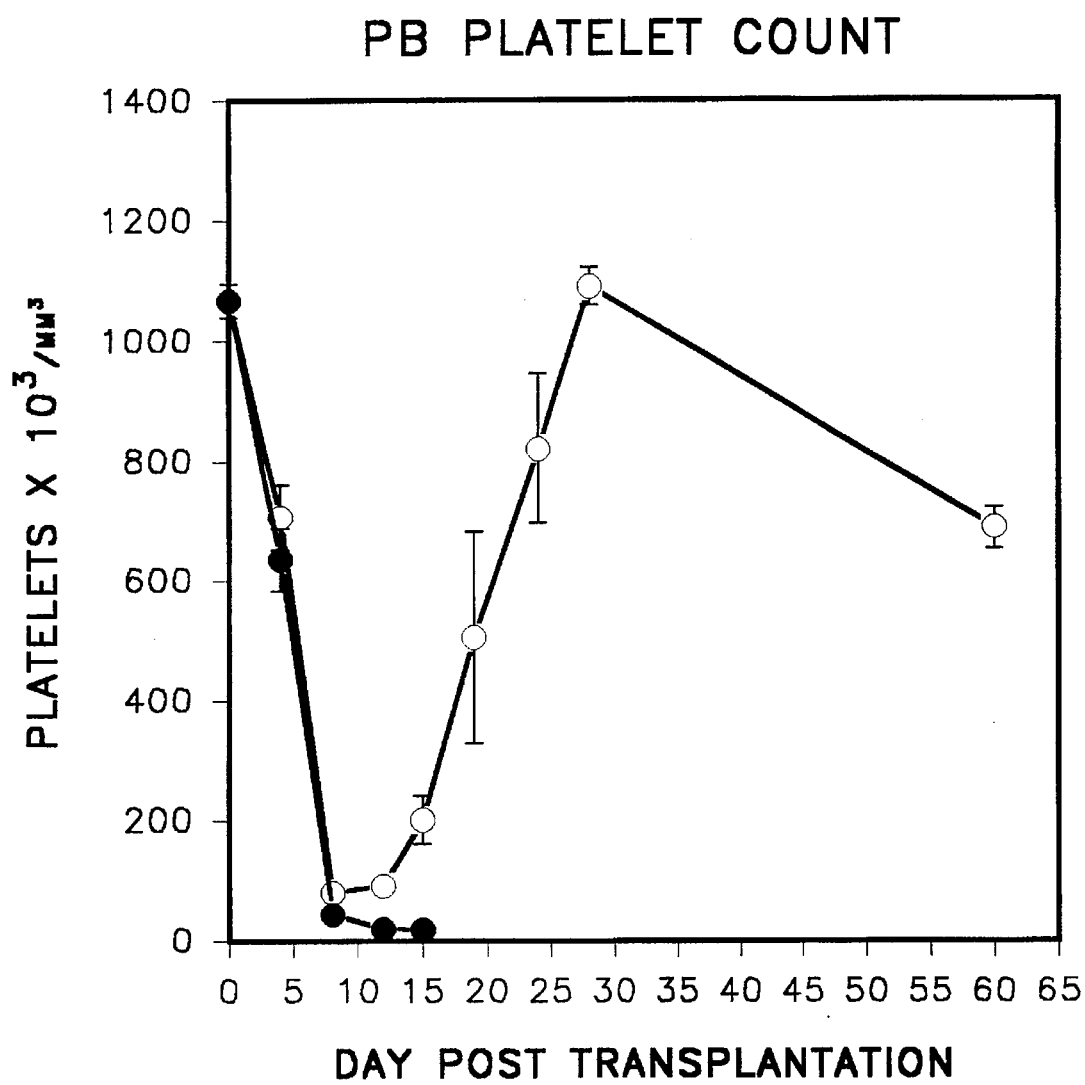
FIG. 9C show the recovery of murine peripheral blood platelet numbers. Mice were exposed to 10.0 Gy of irradiation and administered either $5\times10^4$ bone marrow MNC cells from day-7 liquid suspension cultures treated with GM-CSF+IL-3 (■), or $5\times10^4$ pooled blast cells from day-7 blast cell colonies grown on PMVEC monolayers in the presence of GM-CSF+IL-3 (●). Each point represents the mean±SE of 8 mice from two separate experiments.

The increased progenitor cell activity at the bone marrow and splenic stem cell and progenitor levels ultimately influenced the mature blood cell levels as indicated by an accelerated reappearance of mature white blood cells (WBC), red blood cells (RBC), and platelets (PLT) (FIG. 9) in the peripheral blood. Animals transplanted with $5\times10^4$ pooled blast cells began recovering their number of total white blood cell, neutrophils and platelets between 12 and 15 days after transplantation.

The in vitro amplification/expansion of bone marrow stem cells and progenitor cells on GM-CSF+IL-3 treated PMVEC monolayers increased the number of granulocyte, megakaryocyte and erythroid progenitors as well as the stem cells in the femur and the spleen and therefore hastened the recovery of peripheral blood leukocytes, neutrophils, platelets, and erythrocytes in lethally irradiated host mice.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of expanding human bone marrow $CD34^+$ stem and progenitor cells, including primitive stem cells, in vitro comprising the steps of:
   i) isolating the $CD34^+$ stem and progenitor cells from human bone marrow;
   ii) contacting the isolated $CD34^+$ stem and progenitor cells with porcine microvascular brain endothelial cells; and
   iii) co-culturing the contacted $CD34^+$ stem and progenitor cells and endothelial cells in the presence of at least one cytokine in an amount sufficient to support amplification/expansion of said CD34+ stem and progenitor cells.

2. The method according to claim 1, wherein said $CD34^+$ stem and progenitor cells are contacted with a semi-confluent monolayer of the endothelial cells.

3. The method according to claim 1, wherein said cytokine is selected from the group consisting of a mixture of granulocyte-macrophage colony stimulating factor and stem cell factor; a mixture of interleukin-3, stem cell factor, and interleukin-6; a mixture of granulocyte-macrophage colony stimulating factor, interleukin-3, stem cell factor, and interleukin-6; and combinations of these mixtures.

4. The method according to claim 3, wherein said cytokine is a mixture of granulocyte-macrophage colony stimulating factor, interleukin-3, stem cell factor and interleukin-6.

5. The method according to claim 1, wherein said cytokine is granulocyte-macrophage colony stimulating factor.

6. A method of engrafting human bone marrow $CD34^+$ stem and progenitor cells in a human in need of said $CD34^+$ stem and progenitor cells, said method comprising the steps of:
   i) isolating $CD34^+$ stem and progenitor cells from human bone marrow;
   ii) contacting the isolated $CD34^+$ stem and progenitor cells with porcine microvascular brain endothelial cells containing a factor or factors that expand the $CD34^+$ stem and progenitor cells;
   iii) co-culturing the contacted $CD34^+$ stem and progenitor cells and endothelial cells in the presence of at least one cytokine in an amount sufficient to support amplification/expansion of said $CD34^+$ stem and progenitor cells;
   iv) isolating the amplified/expanded $CD34^+$ stem and progenitor cells from the culture; and
   v) infusing the amplified/expanded $CD34^+$ stem and progenitor cells into said human.

7. The method according to claim 6, wherein said cells are isolated from the bone marrow of the human in need of said $CD34^+$ stem and progenitor cells.

8. The method according to claim 6, wherein said $CD34^+$ stem and progenitor cells are isolated from the bone marrow of a donor.

9. A method of amplifying/expanding human $CD34^+$ bone marrow stem and progenitor cells in vitro which comprises the steps of:
   i) isolating $CD34^+$ stem and progenitor cells from human bone marrow;
   ii) contacting the isolated $CD34^+$ stem cells and progenitor cells with porcine microvascular brain endothelial cells; and
   iii) co-culturing the contacted $CD34^+$ stem cells and progenitor cells and endothelial cells in the presence of a mixture of granulocyte-macrophage colony stimulating factor, interleukin-3, stem cell factor and interleukin-6 in an amount sufficient to amplify/expand said $CD34^+$ stem and progenitor cells.

* * * * *